United States Patent
Sherman et al.

(10) Patent No.: US 6,591,124 B2
(45) Date of Patent: Jul. 8, 2003

(54) PORTABLE INTERSTITIAL FLUID MONITORING SYSTEM

(75) Inventors: Faiz Feisal Sherman, West Chester, OH (US); Francisco Arias, Cincinnati, OH (US); Vladimir Gartstein, Cincinnati, OH (US); Grover David Owens, Fairfield, OH (US); Milan Marcel Jevtitch, Cincinnati, OH (US); Chow Chi Huang, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/853,442

(22) Filed: May 11, 2001

(65) Prior Publication Data

US 2002/0169411 A1 Nov. 14, 2002

(51) Int. Cl.$^7$ ................................................ A61B 5/05
(52) U.S. Cl. ....................... 600/345; 604/19; 604/27; 604/46; 604/48; 600/365; 600/362; 600/578; 600/576; 606/189; 606/186; 606/167
(58) Field of Search .................. 604/27, 46, 19, 604/22, 20, 48; 600/576, 578, 38, 48, 573, 345, 365, 362, 309; 606/189, 186, 167

(56) References Cited

U.S. PATENT DOCUMENTS

| | | | |
|---|---|---|---|
| 3,964,482 A | 6/1976 | Gerstel et al. | |
| 4,055,029 A | 10/1977 | Kalbow | |
| 4,180,232 A | 12/1979 | Hardigg | |
| 4,381,963 A | 5/1983 | Goldstein et al. | |
| 4,585,991 A | 4/1986 | Reid et al. | |
| 4,784,737 A | 11/1988 | Ray et al. | |
| 4,837,049 A | 6/1989 | Byers et al. | |
| 5,134,079 A | * 7/1992 | Cusack et al. | ............... 436/53 |
| 5,156,591 A | 10/1992 | Gross et al. | |

(List continued on next page.)

FOREIGN PATENT DOCUMENTS

| | | |
|---|---|---|
| DE | 196 24 578 A1 | 1/1998 |
| EP | 1 086 719 A1 | 3/2001 |

(List continued on next page.)

OTHER PUBLICATIONS

Mcallister, H., "Micromachined Microneedles for Transdermal Drug Delivery", Allen & Prausnitz, Georgia Institute of Technology, Atlanta, GA.

(List continued on next page.)

*Primary Examiner*—Ira S. Lazarus
*Assistant Examiner*—Tu C. Nguyen
(74) *Attorney, Agent, or Firm*—Bart S. Hersko

(57) ABSTRACT

A strip-like microneedle device is provided that includes an array of hollow microneedles, a diaphragm pump to extract interstitial fluid from skin, and a sensor that detects the concentration of the fluid. The microneedle device can be interfaced to an external sensor to produce a reading, or can be self-contained. One version uses an attachable/detachable microneedle array as a single-use, disposable unit. The device is portable, and is used by placing one finger on the microneedle array, and actuating the diaphragm pump with another finger, thereby obtaining the fluid sample. Solid coated or transparent microneedles could instead be used as an in-situ sensor, with either electrodes or an optical sensor.

30 Claims, 20 Drawing Sheets

U.S. PATENT DOCUMENTS

| | | | |
|---|---|---|---|
| 5,162,043 A | | 11/1992 | Lew et al. |
| 5,198,192 A | * | 3/1993 | Saiton et al. .............. 422/68.1 |
| 5,215,088 A | | 6/1993 | Normann et al. |
| 5,250,023 A | | 10/1993 | Lee et al. |
| 5,256,360 A | | 10/1993 | Li |
| 5,279,544 A | | 1/1994 | Gross et al. |
| 5,318,557 A | | 6/1994 | Gross |
| 5,362,307 A | | 11/1994 | Guy et al. |
| 5,383,512 A | | 1/1995 | Jarvis |
| 5,498,235 A | | 3/1996 | Flower |
| 5,527,288 A | | 6/1996 | Gross et al. |
| 5,551,953 A | | 9/1996 | Lattin et al. |
| 5,591,123 A | | 1/1997 | Sibalis et al. |
| 5,591,139 A | | 1/1997 | Lin et al. |
| 5,611,806 A | | 3/1997 | Jang |
| 5,645,977 A | | 7/1997 | Wu et al. |
| 5,658,515 A | | 8/1997 | Lee et al. |
| 5,676,850 A | | 10/1997 | Reed et al. |
| 5,681,580 A | | 10/1997 | Jang et al. |
| 5,704,520 A | | 1/1998 | Gross |
| 5,711,761 A | | 1/1998 | Untereker et al. |
| 5,730,714 A | | 3/1998 | Guy et al. |
| 5,735,273 A | | 4/1998 | Kurnik et al. |
| 5,771,890 A | | 6/1998 | Tamada |
| 5,800,420 A | | 9/1998 | Gross et al. |
| 5,807,375 A | | 9/1998 | Gross et al. |
| 5,814,020 A | | 9/1998 | Gross |
| 5,820,622 A | | 10/1998 | Gross et al. |
| 5,827,183 A | | 10/1998 | Kurnik et al. |
| 5,848,985 A | | 12/1998 | Muroki |
| 5,848,990 A | | 12/1998 | Cirelli et al. |
| 5,848,991 A | | 12/1998 | Gross et al. |
| 5,855,801 A | | 1/1999 | Lin et al. |
| 5,879,326 A | | 3/1999 | Godshall et al. |
| 5,948,488 A | | 9/1999 | Marecki et al. |
| 6,023,629 A | | 2/2000 | Tamada |
| 6,036,659 A | * | 3/2000 | Ray et al. .................... 600/573 |
| 6,038,465 A | | 3/2000 | Melton, Jr. |
| 6,047,208 A | | 4/2000 | Flower |
| 6,083,196 A | * | 7/2000 | Trautman et al. ............. 604/46 |
| 6,091,975 A | * | 7/2000 | Daddona et al. ............ 600/345 |
| 6,106,751 A | | 8/2000 | Talbot et al. |
| 6,129,696 A | | 10/2000 | Sibalis |
| 6,132,755 A | | 10/2000 | Eicher et al. |
| 6,219,574 B1 | * | 4/2001 | Cormier et al. ............... 604/20 |
| 6,256,533 B1 | * | 7/2001 | Yuzhakov et al. ............ 604/21 |
| 6,312,612 B1 | | 11/2001 | Sherman et al. |
| 6,334,856 B1 | | 1/2002 | Allen et al. |
| 6,375,627 B1 | * | 4/2002 | Mauze et al. ................ 600/584 |
| 6,379,324 B1 | * | 4/2002 | Gartstein et al. ............. 604/22 |
| 6,440,096 B1 | * | 8/2002 | Lastovich et al. ............ 604/27 |
| 6,451,240 B1 | | 9/2002 | Sherman et al. |
| 6,471,903 B2 | | 10/2002 | Sherman et al. |
| 6,494,830 B1 | * | 12/2002 | Wessel ........................ 600/300 |
| 2001/0023324 A1 | * | 9/2001 | Pronovost et al. ........... 600/582 |
| 2002/0006355 A1 | * | 1/2002 | Whitson | |

FOREIGN PATENT DOCUMENTS

| | | |
|---|---|---|
| EP | 1 174 078 A2 | 1/2002 |
| GB | 783479 | 9/1957 |
| GB | 2221394 A | 2/1990 |
| JP | 09051878 A61 B | 2/1997 |
| SU | 1667864 A6 | 7/1991 |
| WO | WO 93/17754 A1 | 9/1993 |
| WO | WO 94/23777 A1 | 10/1994 |
| WO | WO 95/33612 A1 | 12/1995 |
| WO | WO 96/00109 A1 | 1/1996 |
| WO | WO 96/37155 A1 | 11/1996 |
| WO | WO 96/37256 A1 | 11/1996 |
| WO | WO 97/03718 A1 | 2/1997 |
| WO | WO 97/48440 A1 | 12/1997 |
| WO | WO 97/48441 A1 | 12/1997 |
| WO | WO 97/48442 A1 | 12/1997 |
| WO | WO 98/00193 A1 | 1/1998 |
| WO | WO 99/00155 A1 | 1/1999 |
| WO | WO 99/29298 A2 | 6/1999 |
| WO | WO 99/29364 A1 | 6/1999 |
| WO | WO 99/29365 A1 | 6/1999 |
| WO | WO 99/64580 A1 | 12/1999 |
| WO | WO 00/05166 A1 | 2/2000 |
| WO | WO 00/35530 A1 | 6/2000 |
| WO | WO 00/74763 A2 | 12/2000 |
| WO | WO 00/74766 A1 | 12/2000 |
| WO | WO 02/32331 A2 | 4/2002 |

OTHER PUBLICATIONS

Sebastian, H. et al., "Microfabricated Microneedles: A Novel Approach to Transdermal Drug Delivery", Journal of Pharmaceutical Sciences, Aug., 1998, pp. 922–925, vol. 87, No. 8, Atlanta, GA.

Chun, K. et al., An Array of Hollow Microcapillaries for the Controlled Injection of Genetic Materials into Animal/Plat Cells, The University of Tokyo.

Wouters, S. et al., "Microelectrochemical Systems for Drug Delivery", Electrochimica Acta., 1997, pp. 3385–3390, vol. 42, Nos. 20–22.

Prausnitz, M. R., et al, "Transdermal Delivery of Macromolecules: Recent Advances by Modification of Skin's Barrier Properties", Therapeutic Protein and Peptide Formulation and Delivery, pp. 124–153, Chapter 8, ACS Symposium Series 675, Georgia Institute of Technology.

Prausnitz, M. R., et al., Transdermal Transport Efficiency During Skin Electroporation and Iontophoresis, Journal of Controlled Release 38, 1996, pp. 205–217, Massachusetts Institute of Technology, Cambridge, MA.

Papautsky, I. E., et al., "Micromachined Pipette Arrays (MPA)", pp. 2281–2284, Proceedings—$19^{th}$ international Conference—IEEE/EMBS Oct. 30–Nov. 2, 1997, Chicago, IL.

* cited by examiner

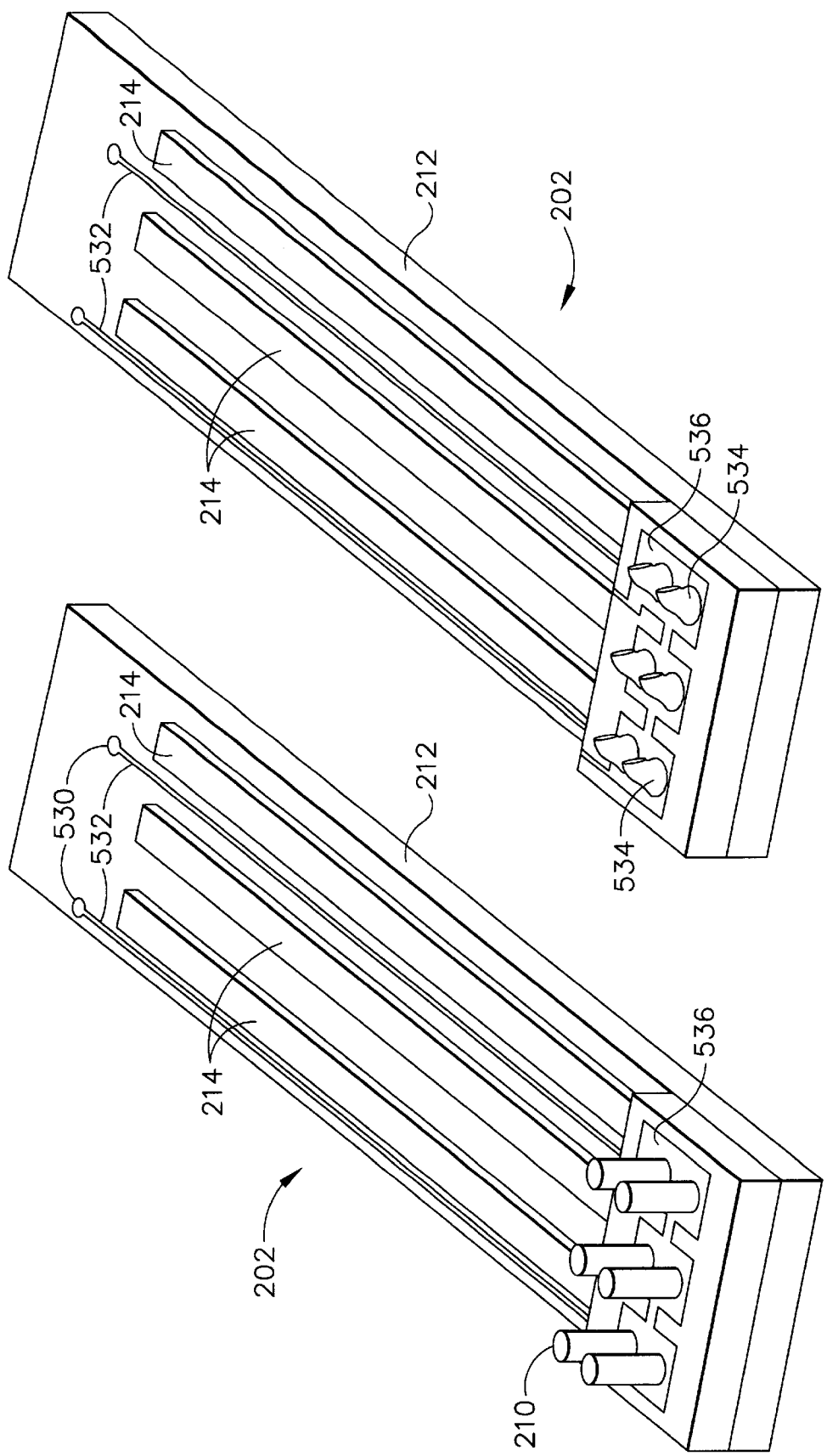

PORTABLE INTERSTITIAL FLUID MONITORING SYSTEM

TECHNICAL FIELD

The present invention relates generally to interstitial fluid monitoring equipment and is particularly directed to a portable glucose monitoring system of the type which could be used at home by consumers. The invention is specifically disclosed as a home glucose monitoring system that uses an array of microneedles to painlessly sample interstitial fluid and provide an indication of the glucose concentration.

BACKGROUND OF THE INVENTION

Topical delivery of drugs and topical sampling of biological fluids are very useful methods for achieving either systemic or localized pharmacological effects, or for diagnostics, although there is a main challenge involved in providing sufficient fluid penetration across the skin. Skin consists of multiple layers, in which the stratum corneum layer is the outermost layer, then a viable epidermal layer, and finally a dermal tissue layer. The thin layer of stratum corneum represents a major barrier for chemical penetration through the skin. The stratum corneum is responsible for 50%–90% of the skin barrier property, depending upon the analyte's water solubility and molecular weight.

An alternative to the use of hypodermic needles for drug delivery by injection is disclosed in U.S. Pat. No. 3,964,482 (by Gerstel), in which an array of either solid or hollow microneedles is used to penetrate through the stratum corneum and into the epidermal layer. Fluid is dispensed either through the hollow microneedles or through permeable solid projections, or perhaps around non-permeable solid projections that are surrounded by a permeable material or an aperture. A membrane material is used to control the rate of drug release, and the drug transfer mechanism is absorption.

Other types of microneedle structures are disclosed in WO 98/00193 (by Altea Technologies, Inc.), and in WO 97/48440, WO 97/48441, and WO 97/48442 (by Alza Corp.). In addition, WO 96/37256 discloses another type of microblade structure. Moreover, WO 99/64580 and WO 00/74763 A2, by Georgia Tech Research Corporation, disclose various microneedle structures and methods for manufacturing the same.

The use of microneedles has one great advantage in that intracutaneous drug delivery or drug sampling can be accomplished without pain and without bleeding. As used herein, the term "microneedles" refers to a plurality of elongated structures that are sufficiently long to penetrate through the stratum corneum skin layer and into the epidermal layer. In general, the microneedles are not to be so long as to penetrate into the dermal layer, although there are circumstances where that would be desirable.

A portable microneedle device that can extract or inspect interstitial fluid from skin and provide an instantaneous readout on a display would be very useful, particularly for diabetics who desire to know in real time their glucose level (concentration). It would be very advantageous to provide one or more self-contained sampling devices based upon microneedles that make available a "microneedle patch" or "microneedle strip" that a human user can touch (with a finger, for example), then press an actuator button or switch to inspect or extract a fluid sample, and finally that automatically display the results, in real time or near-real time. It would be further desirable if the microneedle portions were disposable, designed for a single use.

SUMMARY OF THE INVENTION

Accordingly, it is an advantage of the present invention to provide a fluid sampling apparatus that includes a plurality of microneedles accessible on a first surface, a manually-operated pumping apparatus accessible on a second surface, and a reservoir that is in hydraulic communication with both the microneedles and the pumping apparatus. The reservoir receives fluid that flows through the plurality of microneedles upon manual actuation of the pumping apparatus.

It is another advantage of the present invention to provide a fluid sampling apparatus that includes a plurality of solid, coated microneedles accessible on a first surface, a member having a first end near the coated microneedles and which extends to a second end distal from the coated microneedles, and at least one electrode positioned on the extending member, in which the electrodes are in communication with the coated microneedles. The solid microneedles are coated on an exterior surface, and the coating on the microneedles acts as an electrochemical sensor of a property of a fluid of a biological barrier such as skin. When the solid microneedles make contact with the biological barrier, the electrochemical sensor generates an electrical signal in response to the fluid property.

It is a further advantage of the present invention to provide yet another fluid sampling apparatus that includes an attachable/detachable portion that has a plurality of microneedles, a reservoir, an optical sensor pad, and an optical window; and a main body portion that includes a receptacle to receive the attachable/detachable portion such that, when in position, the optical window faces the main body portion and the plurality of microneedles are accessible, a light source and light detector, and a manually-operated control actuator mounted on a surface of the main body portion that causes fluid to flow proximal to the plurality of microneedles. The reservoir receives fluid that flows through the plurality of microneedles upon manual operation of the control actuator, and the optical sensor pad exhibits a change in a physical property that is detected by the light detector as the light source shines light upon the optical sensor pad.

It is a still further advantage of the present invention to provide still another fluid sampling apparatus is provided, which includes an attachable/detachable portion that has a plurality of microneedles, a reservoir, an electrochemical sensor pad, and at least one electrode in communication with the sensor pad; and a main body portion that includes a receptacle to receive the attachable/detachable portion such that, when in position, the electrodes face the main body portion and the plurality of microneedles are accessible, an electron sensor, and a manually-operated pumping apparatus accessible on a surface of the main body portion. The reservoir receives fluid that flows through the plurality of microneedles upon manual actuation of the pumping apparatus, and the electrochemical sensor pad exhibits a change in a physical property that is detected by the electrodes, which output an electrical signal. The electron sensor is in communication with the electrodes and generates an output signal in response to the electrical signal.

It is still another advantage of the present invention to provide a fluid sampling apparatus that includes a plurality of microneedles and an associated substrate that is in mechanical communication with a manually operable plunger, a housing that contains a variable volume chamber and which contains a flexible membrane that deflects upon movement of the plunger, in which the membrane's deflection causing a variation in the volume of the chamber, and an output port that is in hydraulic communication with the variable volume chamber. Upon actuation of the plunger in one direction, the microneedles are pushed into and pierce a biological barrier such as skin. Upon actuation of the plunger in a second, opposite direction, fluid from the biological barrier is withdrawn into the variable volume chamber and thereby directed to the output port.

It is yet a further advantage of the present invention to provide a replaceable cartridge that includes a plurality of microneedle strips attached to a movable substrate of material; in which each of the microneedle strips includes a plurality of microneedles accessible to a user, a sensor that is in communication with a fluid that flows through the microneedles, and a signal transducer that is in communication with the sensor. The signal transducer of a first of the plurality of microneedle strips generates an electrical signal that is communicated to an output port. The movable substrate or web of material is indexable to a "next" position that will make a second of the plurality of microneedle strips accessible to a user.

It is yet another advantage of the present invention to provide a single-use microneedle system that comprises: an array of microneedle members that protrude from a base member, the microneedle members being of a size, shape, and material so as to penetrate through a stratum corneum of skin when placed against the skin; and a self-destruct mechanism that renders the microneedle members incapable of penetrating the stratum corneum after being operative upon the microneedle members, the self-destruct mechanism comprising one of: (a) a heat source, (b) an electrical energy source, (c) an optical energy source, (d) a chemical reaction, (e) a mechanical member that exerts a force, or (f) a material that permanently encapsulates the microneedle members.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a fluid sampling apparatus is provided, comprising: (1) a plurality of microneedles accessible on a first surface of the fluid sampling apparatus; (2) a manually-operated pumping apparatus accessible on a second surface of the fluid sampling apparatus; and (3) a reservoir that is in hydraulic communication with both the plurality of microneedles and the pumping apparatus. The reservoir receives fluid that flows through the plurality of microneedles upon manual actuation of the pumping apparatus.

In accordance with another aspect of the present invention, a fluid sampling apparatus is provided, comprising: (1) a plurality of solid microneedles accessible on a first surface of the fluid sampling apparatus, in which the solid microneedles are coated on an exterior surface; (2) when the solid microneedles make contact with a biological barrier, the coating on the microneedles acts as an electrochemical sensor of a property of a fluid of the biological barrier, and the electrochemical sensor generates an electrical signal in response to the fluid property; (3) a member having a first end near the coated microneedles and which extends to a second end distal from the coated microneedles; and (4) at least one electrode positioned on the extending member, in which the electrode(s) is/are in communication with the coated microneedles.

In accordance with a further aspect of the present invention, a fluid sampling apparatus is provided, comprising: (1) an attachable/detachable portion that includes a plurality of microneedles, a reservoir, an optical sensor pad, and an optical window; and (2) a main body portion that includes: (a) a receptacle to receive the attachable/detachable portion such that, when in position, the optical window faces the main body portion and the plurality of microneedles are accessible; (b) a light source and light detector; and (c) a manually-operated control actuator mounted on a surface of the main body portion that causes fluid to flow proximal to the plurality of microneedles. The reservoir receives fluid that flows through the plurality of microneedles upon manual operation of the control actuator, and the optical sensor pad exhibits a change in a physical property that is detected by the light detector as the light source shines light upon the optical sensor pad.

In accordance with a yet further aspect of the present invention, a fluid sampling apparatus is provided, comprising: (1) an attachable/detachable portion that includes a plurality of microneedles, a reservoir, an electrochemical sensor pad, and at least one electrode in communication with the sensor pad; and (2) a main body portion that includes (a) a receptacle to receive the attachable/detachable portion such that, when in position, the electrode(s) face(s) the main body portion and the plurality of microneedles are accessible; (b) an electron sensor; and (c) a manually-operated pumping apparatus accessible on a surface of the main body portion. The reservoir receives fluid that flows through the plurality of microneedles upon manual actuation of the pumping apparatus, and the electrochemical sensor pad exhibits a change in a physical property that is detected by the electrode(s), which output(s) an electrical signal. The electron sensor is in communication with the electrode(s) and generates an output signal in response to the electrical signal.

In accordance with a still further aspect of the present invention, a fluid sampling apparatus is provided, comprising: (1) a plurality of microneedles and an associated substrate that is in mechanical communication with a manually operable plunger; (2) a housing that contains a variable volume chamber and which contains a flexible membrane that deflects upon movement of the plunger, in which the membrane's deflection causing a variation in the volume of the chamber; and (3) an output port that is in hydraulic communication with the variable volume chamber. Upon actuation of the plunger in one direction, the microneedles are pushed into and pierce a biological barrier such as skin. Upon actuation of the plunger in a second, opposite direction, fluid from the biological barrier is withdrawn into the variable volume chamber and thereby directed to the output port.

In accordance with a still another aspect of the present invention, a replaceable cartridge is provided, comprising: (1) a plurality of microneedle strips attached to a movable substrate of material, in which each of the microneedle strips includes: (a) a plurality of microneedles accessible to a user, (b) a sensor that is in communication with a fluid that flows through the microneedles, and (3) a signal transducer that is in communication with the sensor. The signal transducer of a first of the plurality of microneedle strips generates an electrical signal that is communicated to an output port. The movable substrate or web of material is indexable to a "next" position that will make a second of the plurality of microneedle strips accessible to a user.

In accordance with a yet a further aspect of the present invention, a single-use microneedle system is provided, comprising: an array of microneedle members that protrude from a base member, the microneedle members being of a size, shape, and material so as to penetrate through a stratum corneum of skin when placed against the skin; and a self-destruct mechanism that renders the microneedle members incapable of penetrating the stratum corneum after being operative upon the microneedle members, the self-destruct mechanism comprising one of: (a) a heat source, (b) an electrical energy source, (c) an optical energy source, (d) a chemical reaction, (e) a mechanical member that exerts a force, or (f) a material that permanently encapsulates the microneedle members.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

FIG. 29 is a perspective view of a microneedle strip that contains an array of microneedles and a set of electrodes, and further includes an electrical circuit that melts the microneedles after a single use by a user, as constructed according to the principles of the present invention.

FIG. 30 is a perspective view of microneedle strip of FIG. 29, in which the microneedles have been deformed by application of heat via an electrical current, such that the microneedles cannot be re-used.

DETAILED DESCRIPTION OF THE PREFERRED EMBODIMENT

Figure 1:
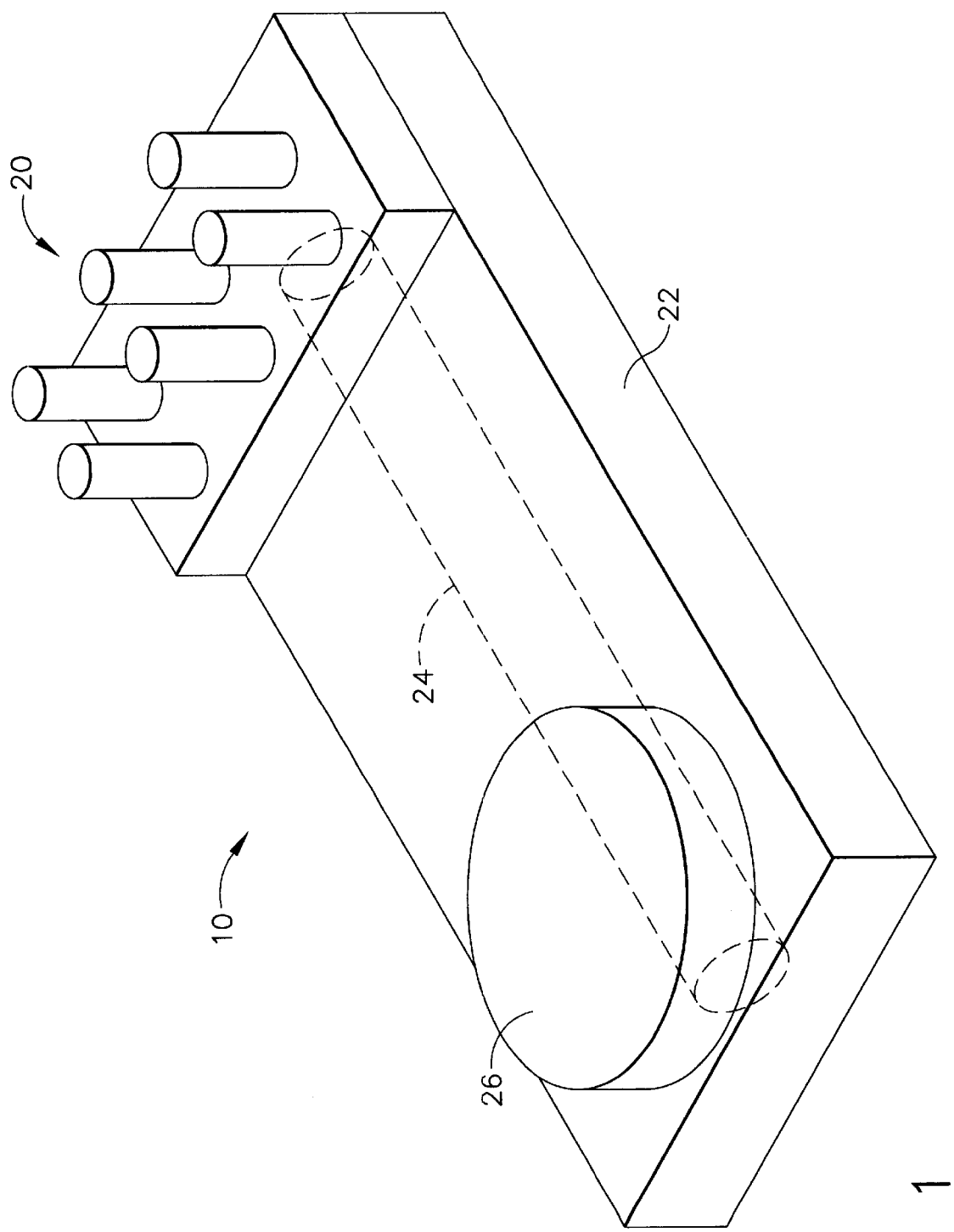
FIG. 1 is a perspective view of a microneedle strip that contains a microneedle array, a diaphragm pump, and an fluid channel, as constructed according to the principles of the present invention.

Reference will now be made in detail to the present preferred embodiment of the invention, an example of which is illustrated in the accompanying drawings, wherein like numerals indicate the same elements throughout the views.

A strip-like microneedle device is provided in which an array of hollow microneedles is disposed on one end, a diaphragm pump is disposed on an opposite end, with a fluidic channel therebetween. A person would place one finger on the microneedle array from one hand, and use the other hand to hold the diaphragm pump in place. Once both fingers are in place from both hands, the diaphragm pump is actuated to extract fluid through the microneedle array from the person's finger. Once the fluid has been extracted, it accumulates in a chamber adjacent to the diaphragm pump, which includes a one-way valve to retain that fluid.

A sensor or signal transducer is used to convert the concentration of a fluid of interest into an electrical signal, which can be analyzed by an external sensor or display unit. Various types of sensors can be used for this purpose, including for example: an electrochemical sensor, a chemiluminescent sensor, a photochemical sensor. Certainly other types of transducers could be used that generate an electrical output signal.

An alternative microneedle array embodiment utilizes a one-hand unit in which the microneedle array is mounted on a top surface of the unit, the diaphragm pump is mounted on the bottom surface of the unit, and a reservoir is disposed in a volumetric space therebetween. A person can place a finger or arm, for example, on the microneedles, an opposable thumb (from the same hand) on the diaphragm pump, and while pressing the finger and thumb together, extract interstitial fluid from the finger through the microneedles. The fluid is stored in the reservoir for further processing by an electrochemical or optical sensor.

Another microneedle strip sensor is provided in which both the microneedles and the diaphragm pump are disposed on one end of the strip, and can be handled by a single hand of a person. Electrodes are disposed along the strip, and are in electrical communication with a sensor pad that is disposed near a fluidic chamber between the diaphragm pump and the microneedles. Once the person actuates the diaphragm pump, interstitial fluid is extracted through the microneedles and the sensor pad, which causes an electrical signal to occur along the electrodes. An external electron sensor can be placed into contact with the electrodes via a fluidic output port to provide a display output.

A solid microneedle array embodiment is provided in which an array of solid microneedles is disposed on one end of a microneedle strip, and this array of solid microneedles is coated with a special material. This special coating material essentially converts the solid microneedles into an electrochemical sensor, which generates an electrical signal that is sent to a set of electrodes. These electrodes can then be placed into electrical contact with an external electron sensor to provide a display output. This is referred to as in-situ sampling. This in-situ device alternatively can be placed within a total package that contains a display, rather than utilizing an external sensor.

A two-part self-contained microneedle sensor is provided as another alternative embodiment. In this embodiment, the main portion of the sensor includes a pushbutton manual actuator, a display, a light source, an optical detector, and a controller that measures the input signal and causes the display to indicate a reading. A second, detachable portion includes an array of microneedles, a diaphragm pump, and a fluidic chamber that is in communication with an optical sensor pad. The microneedle portion includes a "color interrogation window" that allows light from the light source to shine into the fluid chamber and directly into the extracted interstitial fluid. The reflected light from the interstitial fluid then travels back through the window and to the optical detector or sensor. A change in wavelength will occur according to variations in the concentration of a fluid of interest within the interstitial fluid. The microneedle portion of this self-contained unit is disposable, and easily detachable once the extracted fluid has been sampled. A new, unused microneedle array is then pre-loaded into the bottom of the larger sensing unit. This unit can have a diaphragm pump that is spring-loaded or otherwise cocked so that the top pushbutton actuator begins in a lower position and, once actuated, can pop into an upper or raised position to extract the fluid through the microneedles.

Another similar embodiment of a self-contained microneedle sensor utilizes a set of electrodes and an electrosensor pad that makes contact with the electrodes. The electrosensor pad acts as an electrochemical sensor that induces a current or voltage in the electrodes. The pad and the electrodes are part of the disposable microneedle array portion of the overall sensing unit, along with a diaphragm pump. The non-disposable portion of the sensor includes the pushbutton manual actuator, a display, interface electronics, and a controller that measures the input signal and causes the display to indicate a reading. The diaphragm pump could be spring-loaded or could be cocked such that, once actuated, it will pop up and extract the fluid through the microneedle array.

A continuous measurement microneedle sensing system is also provided as a further alternative embodiment. In this embodiment, the diaphragm is deformable and is attached to a plunger that pushes the microneedle array into the skin to make openings in the skin for later extraction of interstitial fluid. When the pump/diaphragm top "button" portion is released, the plunger rises and brings up the microneedle array out of the skin. At this time, interstitial fluid is withdrawn and placed into a volumetric chamber. This chamber is in communication with a hollow tube that will withdraw a sample of the interstitial fluid into a separate electronic unit that will sample and read the concentration of the fluid. This separate electronic unit also includes a display that can provide a reading in engineering units of the concentration of the fluid of interest.

The sensor can remain on the skin for hours, or perhaps even days. The microneedle array can be used in three ways: (1) it can be pressed into the skin where it remains for the entire prescribed sampling duration; (2) it can be pushed down into the skin upon each sample that is to be taken; or (3) if the holes are sufficiently large from the initial impression into the skin by the microneedles, then after the microneedles are withdrawn, the interstitial fluid will continuously remain in the chamber for sampling at any desired time by the separate electronic unit through the hollow tube.

An alternative embodiment would use solid microneedles that have a coating that will convert the microneedles into an electrochemical sensor. In that embodiment, the microneedles would likely have to be inserted into the skin each time a new reading is to be taken, or left in the skin for continuous readings over the prescribed time.

The microneedle strips can be supplied in a disposable cartridge form if desired, and one such disposable cartridge could use a web or tape containing multiple microneedle strips that plugs into a personal data assistant, such as a palm pilot. This plug-in cartridge will contain a source reel and take-up reel, which advances a web or tape containing individual microneedle strips at predetermined intervals. The strips will index to a location near a hole, through which a person's finger can be placed and made to contact the microneedle array. At this time, interstitial fluid can be withdrawn, or otherwise detected if the microneedles are solid. The plug-in cartridge would preferably include a microprocessor with an A/D converter to provide a binary (digital) or serial signal through a connector into the PDA unit.

Another self-contained microneedle sensing device could use a refill cartridge that snaps into the bottom of the unit, and which ejects spent patches or strips of microneedles after they have been utilized to extract fluid. This device could include a button that will advance the microneedles and take the sample, and also would preferably include a display so the person can get a direct reading of the concentration of a fluid of interest.

A further embodiment of a self-contained microneedle sensor unit includes a disposable refill cartridge that uses a source reel and take-up reel that is similar to the plug-in cartridge used with a palm pilot, described above. In this new embodiment, the unit is a dedicated sensing device which provides a hole for the microneedle patch or strip, and a display with electronics to provide information in engineering units or percent of the concentration of a fluid of interest. A source reel and tape-in reel are provided, which rotate to index the strips appropriately.

A still further embodiment of a disposable set of microneedle strips uses a rotatable disk that has multiple microneedle strips thereupon. The overall self-contained microneedle sensor housing can be opened, so that its top portion flips up along a hinge and allows access for removing a previously-used disposable disk, and for inserting a new such disposable disk that contains unused microneedle patches or strips. The top is then closed and a finger hole is used for placement of a finger against a microneedle strip or patch. At that time, the sample is extracted and a display will provide the concentration information in engineering units.

The microneedles of the present invention can also be constructed in a manner so as to operate as a "single-use" device, in which the microneedles themselves are effectively destroyed after their initial (and sole) use. They essentially self-destruct after this initial use, and various methodologies to implement this destruction are available. Two relatively simple methodologies are either to mechanically crush the microneedles or to melt them. A chemical treatment of them is a third possibility. The microneedles do not literally need to be entirely destroyed; it is sufficient to shorten their length or to otherwise deform their tips or side wall structures so that they cannot again penetrate the stratum corneum of skin.

If heat is to be used to destroy the microneedles, the heat source could be radiation (e.g., an electric lamp or laser light source aimed at the microneedles) or it could be electrical (e.g., an electrical heating element near the microneedles). The melting action would preferably greatly deform the microneedles, while at the same time causing their length to shorten. Of course, sufficient heat could be applied to melt them completely down, or even to vaporize them if that is really desirable.

If mechanical action is to be used to destroy the microneedles, this could be done by a pivotable crushing action, or by a shear force. If a shear force is used, the mechanical action could be provided by a moving web of material to which the microneedles are attached, and the microneedles would bump against a protrusion that would cause them to either break or significantly bend.

By modifying the condition of the microneedles so as to be essentially non-usable, their re-use can be prevented. This reduces the risk of accidental repeated insertion.

The destructive means to deform or crush the microneedles can be included in a plug-in cartridge that contains multiple microneedle patches on a moving web or rotatable disk. In this configuration, the microneedle patches index to an opening where the user can touch the microneedle patch, and after this occurs, the patches further index to a station or position where the self-destruction action is accomplished. In this manner, the microneedle patches are automatically destroyed or disabled so as to prevent their re-use.

Another preferred embodiment of the present invention involves the application of heat at the microneedle tips to facilitate interstitial fluid extraction, or to provide a chemical enhancement at the microneedles to either assist in sensing of interstitial fluid or to facilitate interstitial fluid extraction. For example, an electrical current can be directed through the tips of microneedles while they are inserted in the stratum corneum of skin, which will produce heat energy in tips that are made of an electrically conductive material, or of an electrically semiconductive material. Another example is to coat solid microneedles with a chemical that can absorb some of the interstitial fluid, or to coat hollow microneedles with a chemical that will facilitate movement of interstitial fluid through a channel of the microneedles toward an electrochemical sensor.

Referring now to the drawings, an interstitial fluid sampling system is illustrated in FIG. 1, and is generally designated by the reference numeral 10. On one end of the sampling system 10 is an array of microneedles 20, which in this embodiment preferably are hollow microneedles or "microtubes." On the opposite end of the sensing device 10 is a diaphragm pump 26 that is associated with a one-way valve (not shown). A fluidic channel 24 runs through the main body 22 of the sampling device 10, and connects the diaphragm pump 26 to the microneedles 20 hydraulically.

Figure 2:
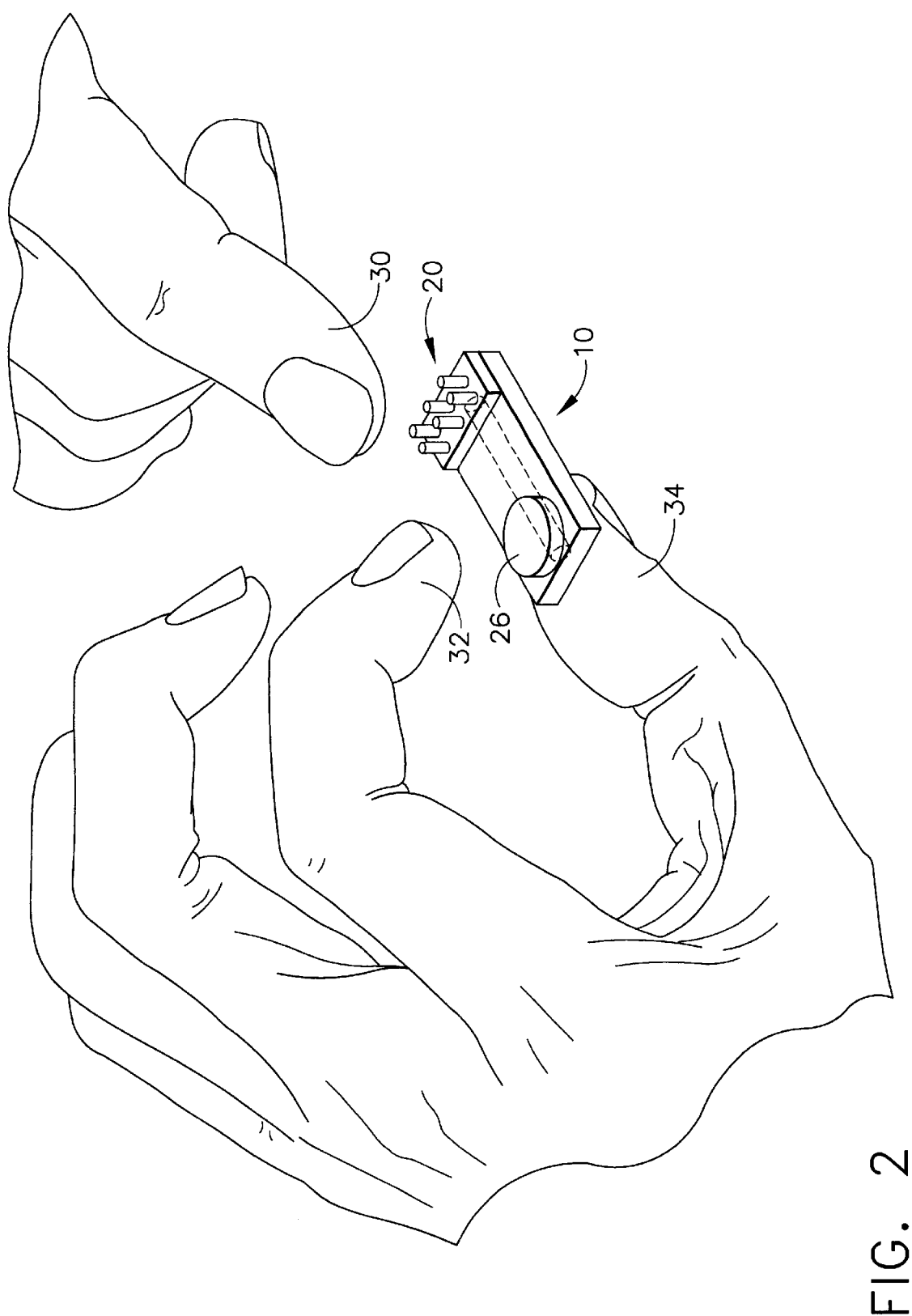
FIG. 2 is a perspective view of the microneedle strip of FIG. 1, while being actuated by a person's hand.

The method for sampling the interstitial fluid is illustrated in FIG. 2. A person's index finger at 30 is pressed against the tips of the microneedle array 20, while the other person's hand is used to hold the far end of the apparatus 10, using the other index finger 32 and the opposable thumb 34. While the person's first hand (or finger) 30 is pressed against the microneedles 20, the other hand is used to press the diaphragm pump 26 by way of the other index finger 32 being pressed against the thumb 34 that is in opposition to the pressing motion of the finger 32.

When the diaphragm 26 is pressed and released, it creates pressure in the interior chamber (not shown) inside the diaphragm area 26, and this pressure will tend to withdraw interstitial fluid from the other index finger 30 through the hollow microneedles 20. In this instance, the pressure being created by the diaphragm 26 is negative pressure with respect to atmospheric pressure, or at least with respect to the body interstitial fluid pressure. The number of "pumps" made by the finger 32 against the diaphragm 26 could be adjusted, depending upon the volume of interstitial fluid that is desired to be withdrawn from the finger 30.

It will be understood that animal skin represents a "biological barrier" that generally prevents transfer of fluids between its inner layers and its external environment. In human skin, the stratum corneum is very good at preventing such fluid transfer. The microneedles are designed to penetrate through the stratum corneum, and thereby drastically increase the permeability of the skin at this area. These concepts are well known in the prior art.

It will be further understood that other areas of the skin could be used as the target for the microneedle array instead of the fingers that were described in the above examples. In fact, other areas of the skin would likely have a thinner stratum corneum layer, and thus be easier to penetrate. As an example, the microneedle array 110 of either FIGS. 5 or 6 could be pressed onto a human forearm (see FIG. 5A), and only a single hand or finger would then be needed to actuate the diaphragm 116.

Figure 3:
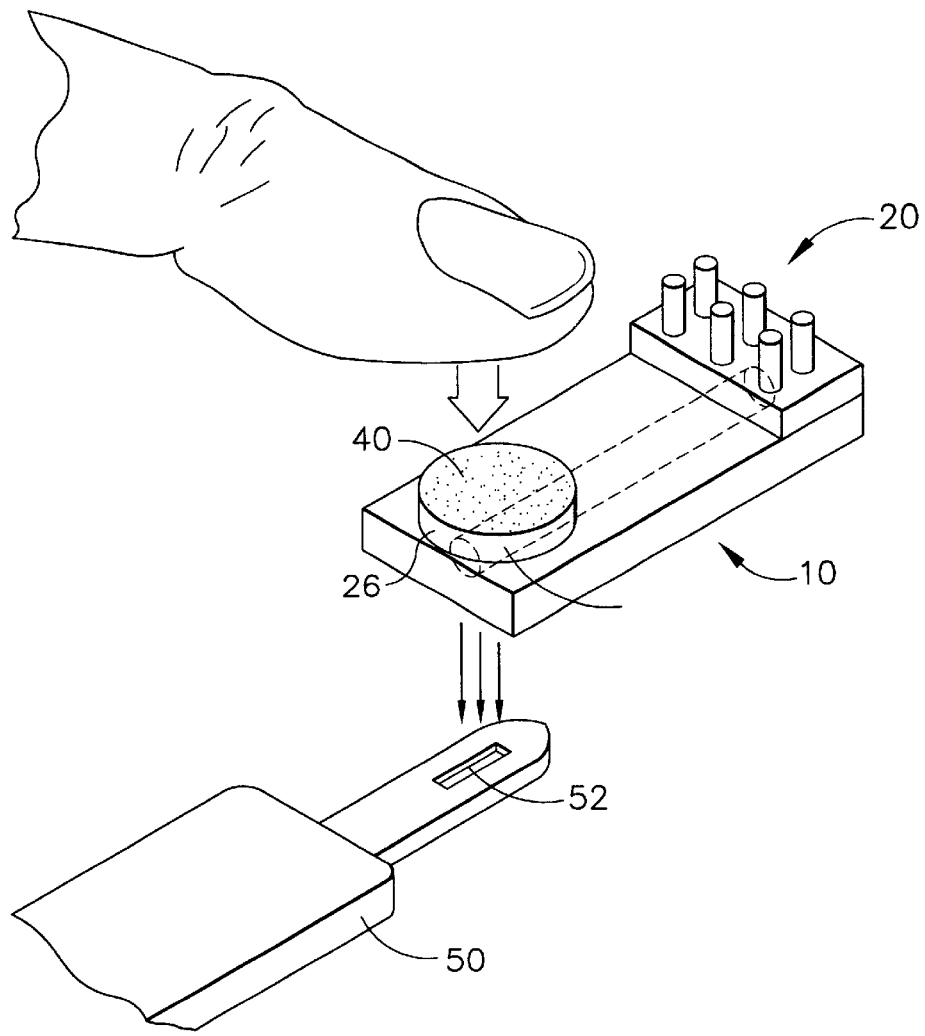
FIG. 3 is a diagrammatic view of the microneedle strip of FIG. 1, while a sample is being tested by an external sensor.

Once the fluid sample has been extracted as according to the methodology illustrated in FIG. 2, the fluid sample can then be tested, as illustrated in FIG. 3. The interstitial fluid is now within the diaphragm's associated volumetric space, as depicted at the reference numeral 40. The one-way valve (not shown) causes this fluid to remain in this volumetric space 40, even after the person's other finger 30 has been removed from the microneedles 20. An external sensor at 50 is then put into fluidic contact with a certain area near the diaphragm 26 of the sensing device 10. This area is referred to as a fluidic output port, or hydraulic output port, which allows the external sensor 50 to receive a sample of the extracted fluid from the volumetric space 40.

When the external sensor 50 is in its proper position, the diaphragm pump 26 can again be actuated by a person's index finger to send a dose of the interstitial fluid to the external sensor 50. This external sensor 50 has a sensing transducer 52 near the tip of the external sensor 50. Such devices are commercially available, and are sometimes referred to as "strip sensors." In some commercial external sensors, the sensing element will contain glucose oxidase, which will react with the glucose concentration in the interstitial fluid sample that was extracted in the process of FIG. 2.

The commercial sensors available include electron sensors in which the sensing element 52 acts as an electrochemical sensor or a sensor having electrodes. This external sensor 50 could also include some type of indication device, such as a digital display or a series of colored lights, such as LED's (light emitting diodes) that could visually indicate predetermined ranges of (e.g.) glucose concentration.

As an alternative to using an electrochemical sensor, an optical sensor could be used. Such an optical sensor could be made in two parts, in which the first part reacts to a change in the electromagnetic energy properties, such as a change in wavelength (e.g., of reflected light), upon the variation in glucose concentration. The second part of the optical sensor would then be an optical detector that measures photons, and specifically looks for photons exhibiting the new wavelength of interest in the fluidic sample or in the reactive first part of the sensor.

It will be understood that the display or "strip sensor" that is provided with the external sensor 50 could be integrated into the fluidic sampling device 10 as a unitary structure. Such unitary structures are described below. On the other hand, it will also be understood that the sample having its concentration measured could remain in the diaphragm's volumetric space at 26, in which the contained sample could be moved to a remote site and tested with a separate sensor at the remote site.

Figure 4:
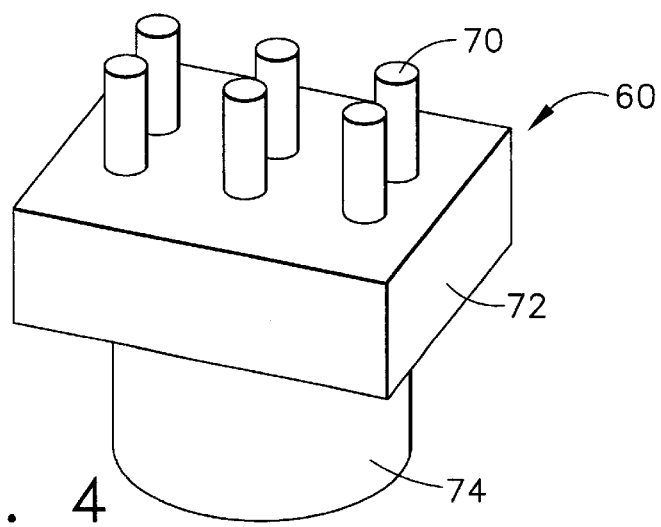
FIG. 4 is a perspective view of a one-hand microneedle fluid-extracting device which contains a microneedle array, a diaphragm pump, and an internal sensor pad, as constructed according to the principles of the present invention.

The first embodiment 10 of a interstitial fluidic extraction apparatus is a two-hand device. A similar device could be made such that only a single hand would be used, as illustrated in FIG. 4. FIG. 4 depicts a fluid sample extraction apparatus generally designated by the reference numeral 60, having a main body portion 72, an array of hollow microneedles 70 on its top surface (as seen in FIG. 4), and a diaphragm pump 74 portion on its opposite or bottom surface. This arrangement renders the extracting apparatus 60 into a one-hand operable device, and also creates a smaller physical device that eliminates the fluidic channel 24 that was part of the first embodiment sample extraction apparatus 10, viewed in FIG. 1.

A person's index finger could be placed on the microneedle array 70, while his or her opposable thumb is placed on the diaphragm pump 74. When the interstitial fluid sample is desired, the person actuates (e.g., presses and releases) the diaphragm pump 74 to cause fluid to be evacuated from the person's index finger through the hollow microneedle 70. The diaphragm pump would have a reservoir volumetric space to hold the interstitial fluid for later sample testing.

This reservoir (not shown, but within the body 72) could be essentially empty, containing only air or some inert gas; or the reservoir could contain a liquid, such as a saline solution. Another alternative is to have a diaphragm that is "primed" or pre-bent, and once pressed, the button-shape of the outer perimeter of the diaphragm pump would release by popping out to a further extent than at its initial position. Other optional design configurations could easily be utilized within the present invention illustrated in FIG. 4.

As in the first embodiment 10 illustrated in FIG. 1, the diaphragm pump would preferably have some type of one-way valve to retain the interstitial fluid within the reservoir once it is withdrawn from the person's finger. Furthermore, multiple "pumps" of the diaphragm pump 74 could be utilized to extract greater volumes of fluid, if desired. Electrical contacts that act as electrodes could be used as the output sensing indication for making contact with an external sensor, such as the electron sensor 50 illustrated in FIG. 3.

Some terminology that will be found in this patent document will include the phrase "microneedle strip" which refers to a configuration similar to that illustrated in FIG. 1, depicting the first embodiment 10. This first embodiment includes the microneedle array 20, diaphragm pump 26, and a strip-like body 22 having the fluidic channel 24. Another example term found in this patent document will be the word "patch" (or the term "microneedle patch"), which generally will refer to the microneedle array itself. This would refer to both the microneedle array 20 illustrated in FIG. 1, and also the microneedle array 70 illustrated in FIG. 4. These microneedle array structures 20 and 70 could have identical configurations and materials, or if desired, they could be of different dimensions or materials, depending upon the specific application to be used when withdrawing or discharging fluids.

Figure 4A:
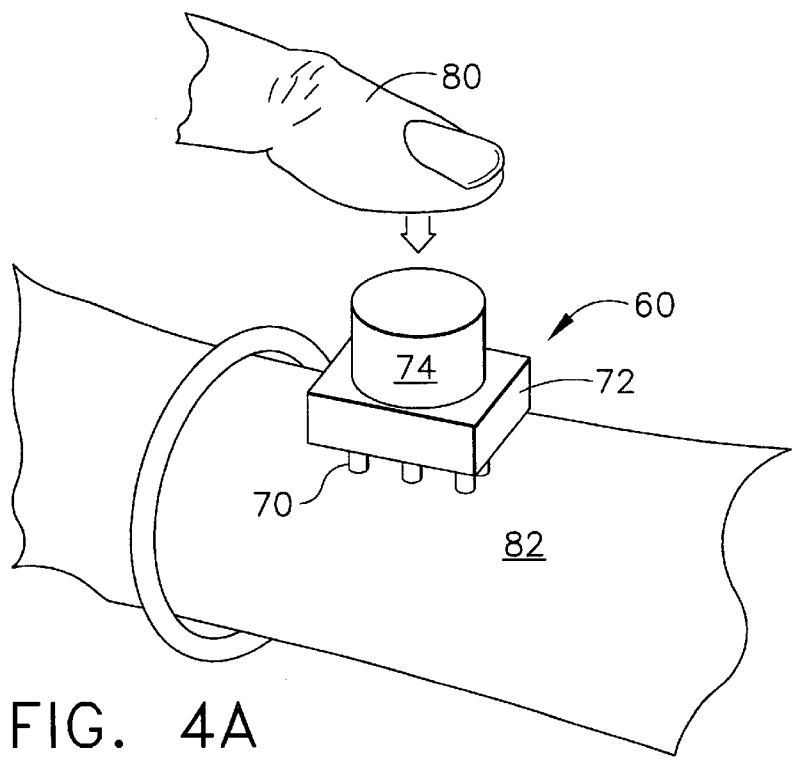
FIG. 4A is a perspective view of the microneedle fluid-extracting device of FIG. 4, depicted as being used against a human arm.

FIG. 4A depicts the use of the fluid sample extraction apparatus 60 on the surface of a human arm—or forearm, near the wrist, in this instance. The finger 80 is used to depress the diaphragm pump 74, while the microneedle array 70 is pressed into the skin of the arm 82. It will be understood that the microneedle arrays of the present invention can be placed virtually on any area of the skin of an animal (or even plants for that matter), without departing from the principles of the present invention. Certainly the stratum corneum of the skin on the inside forearm will almost always be thinner than that on the fingers (especially where calloused), and thus easier to penetrate by the microneedles.

Figure 5:
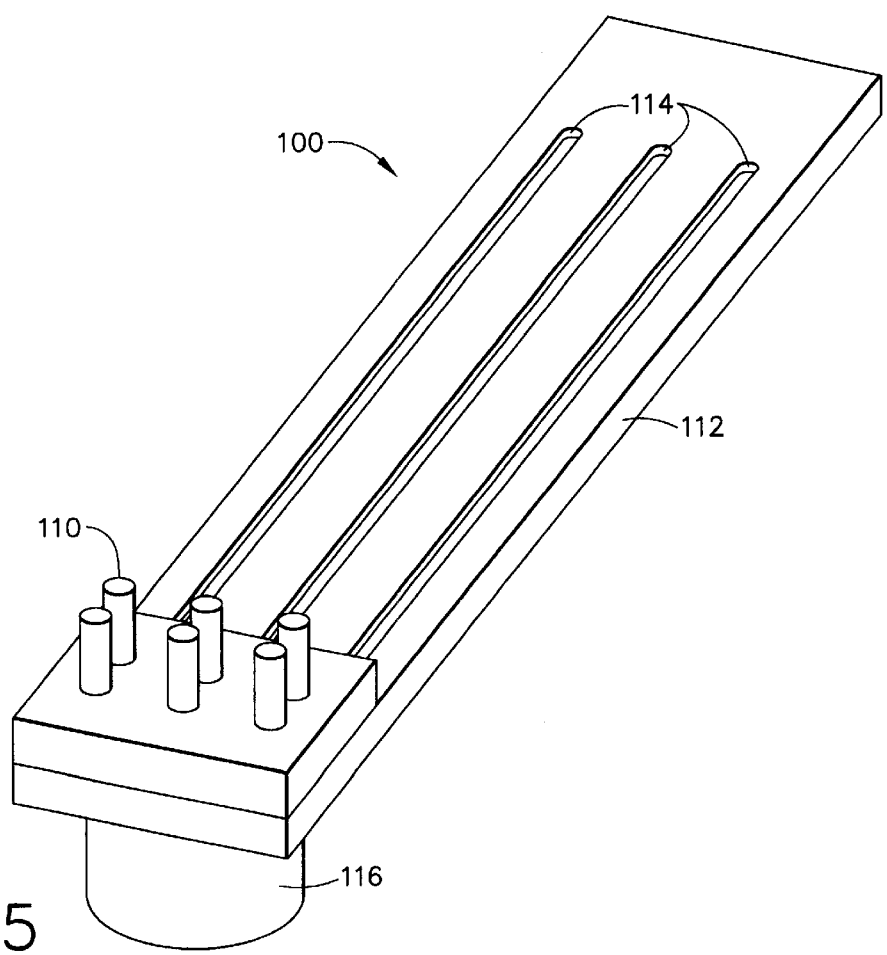
FIG. 5 is a perspective view of a microneedle strip that includes a microneedle array, a diaphragm pump, a fluidic chamber with a sensor pad, and a set of electrodes, as constructed according to the principles of the present invention.

FIG. 5 illustrates another strip-like sensing device, and in this instance it not only extracts interstitial fluid but also includes a sensing device to provide an indication as to the fluid concentration. The overall apparatus is generally depicted by the reference numeral 100, and includes a main body 112 that contains three electrodes 114, and on one end contains a microneedle array 110 and a diaphragm pump 116, which is on the opposite surface from the microneedle array 110. A "sensor pad" 120 is disposed such that it makes contact with electrodes 114, and is in a position essentially between the microneedles 110 and the fluidic chamber adjacent to the diaphragm pump 116 (see FIG. 6).

The microneedle array 110 is mounted to, or an integral part of, a body or substrate portion 124, and the fluidic chamber is within the other half of this main body 122, between the sensor pad 120 and the diaphragm pump 116. In one preferred embodiment, the sensor pad 120 is a porous membrane that is made of a particular chemical, or includes a certain chemical that converts the sensor pad into an electrochemical sensor. For example, the porous membrane of the sensor pad 120 could be made of or include glucose oxidase, which will react with an electrical response to concentration variations in glucose of the interstitial fluid that is withdrawn from a person's skin by use of the microneedles 110 and the diaphragm pump 116.

Figure 5A:
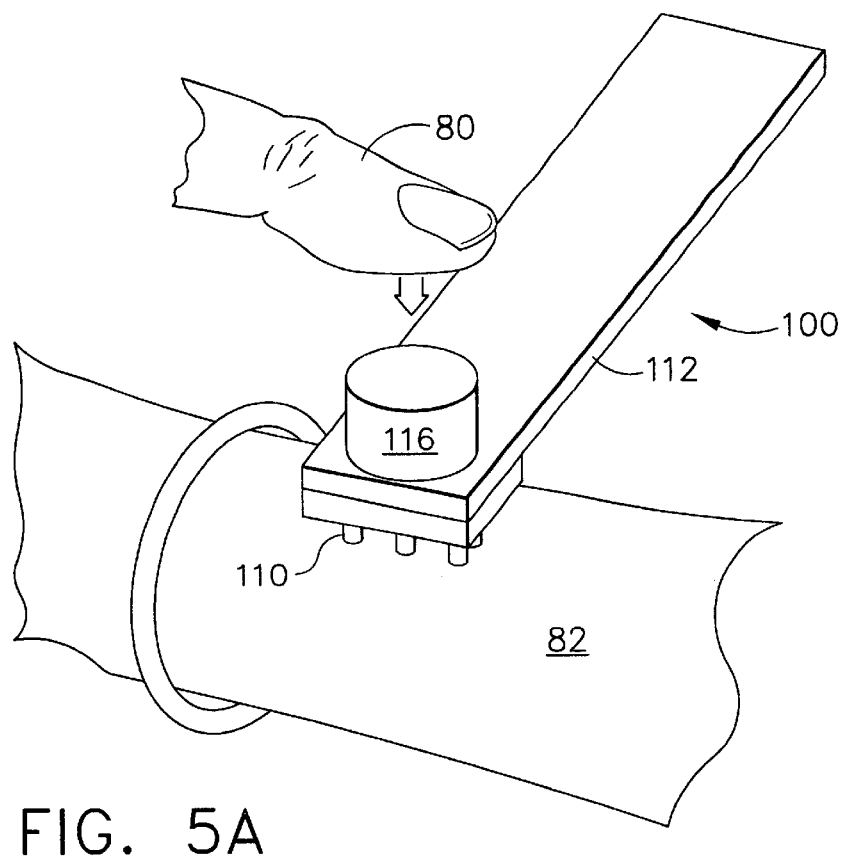
FIG. 5A is a perspective view of the microneedle fluid-extracting device of FIG. 5, depicted as being used against a human arm.

FIG. 5A depicts the use of the strip-like sensing device 100 on the surface of a human arm—or forearm, near the wrist, in this instance. The finger 80 is used to depress the diaphragm pump 116, while the microneedle array 110 is pressed into the skin of the arm 82. It will be again understood that the microneedle arrays of the present invention can be placed virtually on any area of the skin of an animal (or even plants for that matter), without departing from the principles of the present invention. Certainly the stratum corneum of the skin on the inside forearm will almost always be thinner than that on the fingers (especially where calloused), and thus easier to penetrate by the microneedles.

Figure 6:
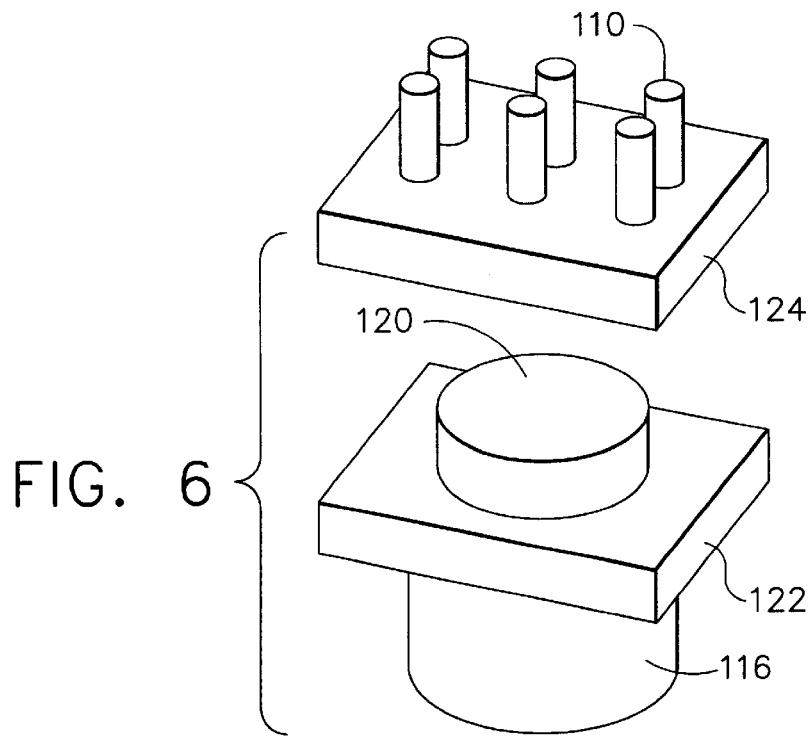
FIG. 6 is an exploded view of a portion of the microneedle strip of FIG. 5.

The diaphragm pump 116 could be eliminated in favor of a mere reservoir, and the interstitial fluid could flow by means of capillary force alone. The microneedles would direct this fluid onto the sensor pad by a wicking action, for example. Such a device could nevertheless have the appearance as illustrated in FIG. 6, although the structure referred to by the reference numeral 116 would represent only a reservoir. The alternative structures of FIGS. 4 and 5 could also operate by capillary action, and thus not require a diaphragm pump at 116.

Figure 7:
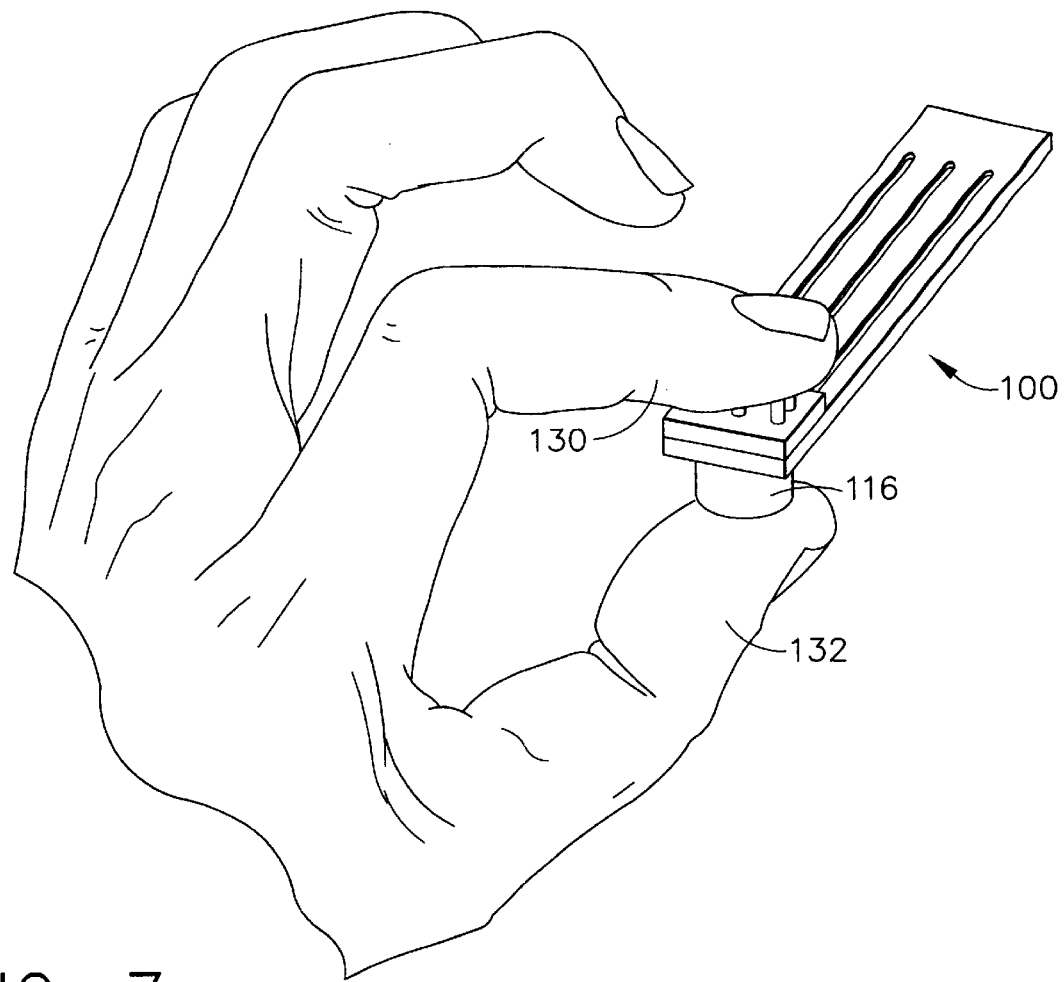
FIG. 7 is a diagrammatic view of the microneedle strip of FIG. 5 while it is being actuated by a person's hand.

FIG. 7 shows how a person's fingers are used in a one-hand operation to place one finger on the microneedles and a different finger against the diaphragm pump. On FIG. 7, the microneedle strip 100 is held between a person's index finger 130 and the person's opposable thumb 132, in which the thumb 132 presses against the diaphragm pump exterior at 116, while the microneedles 110 are in contact with the person's index finger 130.

Figure 8:
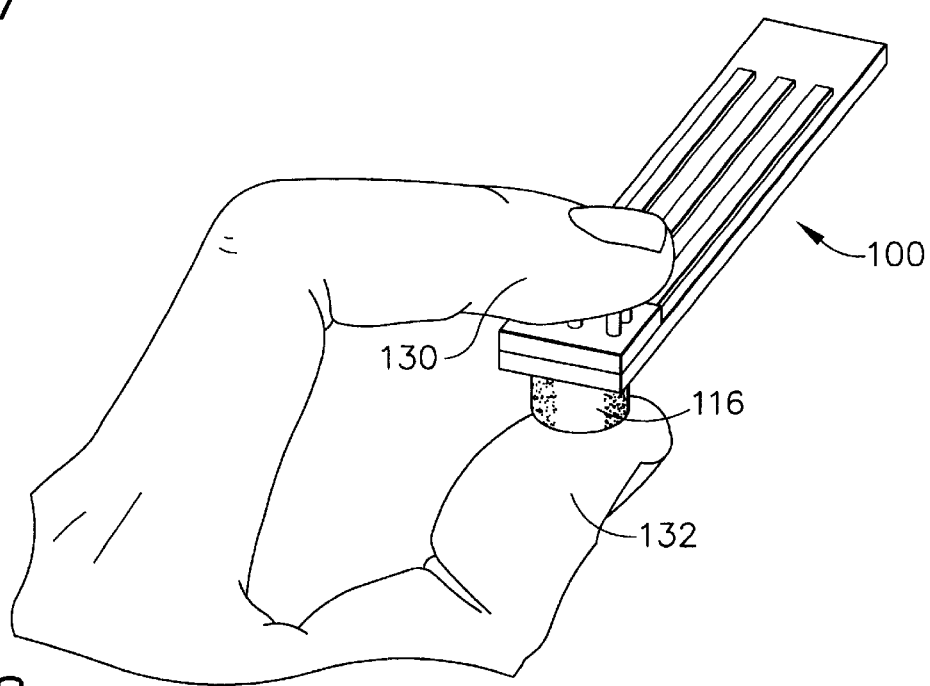
FIG. 8 is a diagrammatic view of the microneedle strip of FIG. 5 after a fluid sample has been taken, and while still being held in place by a person's hand.

The person/user exerts pressure against the diaphragm pump 116 and thereby causes interstitial fluid in the finger 130 to be extracted through the hollow microneedles 110, and into the reservoir (not shown) that is within the body portion 122, near the diaphragm 116. Depending upon how large a volume of fluid is required for a particular application, the person could use their thumb 132 to pump only a single time against the diaphragm 116, or there could be multiple pumping operations under certain circumstances. Once the interstitial fluid is withdrawn through the microneedles, some type of one-way valve mechanism could be used to retain the fluid within the reservoir and the person could thereby withdraw their finger 130 from the microneedles and have this interstitial fluid retained within the reservoir. This is diagrammatically shown in FIG. 8, which shows that the diaphragm and reservoir portion of the microneedle strip 100 has been filled with the interstitial fluid. As in the microneedle strip 10 or the microneedle structure 60, the reservoir could initially be empty, filled with air or an inert gas, for example, or the reservoir could be filled with some type of liquid, such as a saline solution.

Figure 9:
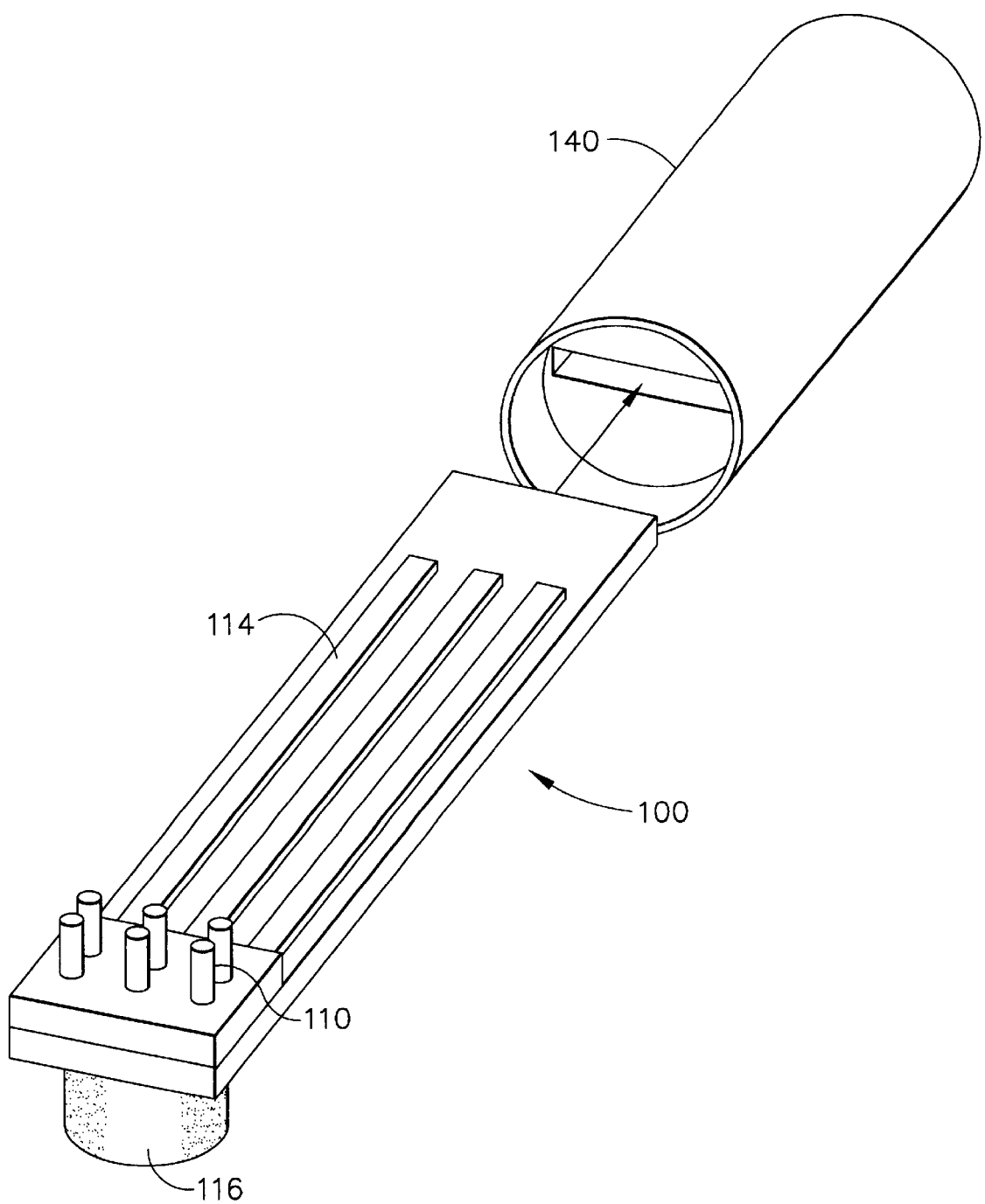
FIG. 9 is a diagrammatic view of the microneedle strip of FIG. 5 while it is connected to an external sensor.

In FIG. 9, an external sensor device 140 is brought into contact with the electrodes so as to directly interface with the electrodes 114. In this situation, the external sensor 140 would preferably act as an "electron sensor" that can provide an output or a display that directly indicates the concentration of the interstitial fluid that has caused the electrodes to receive a particular current charge or small voltage. Such external electron sensors are available commercially, and some of these commercial units include a display.

Figure 10:
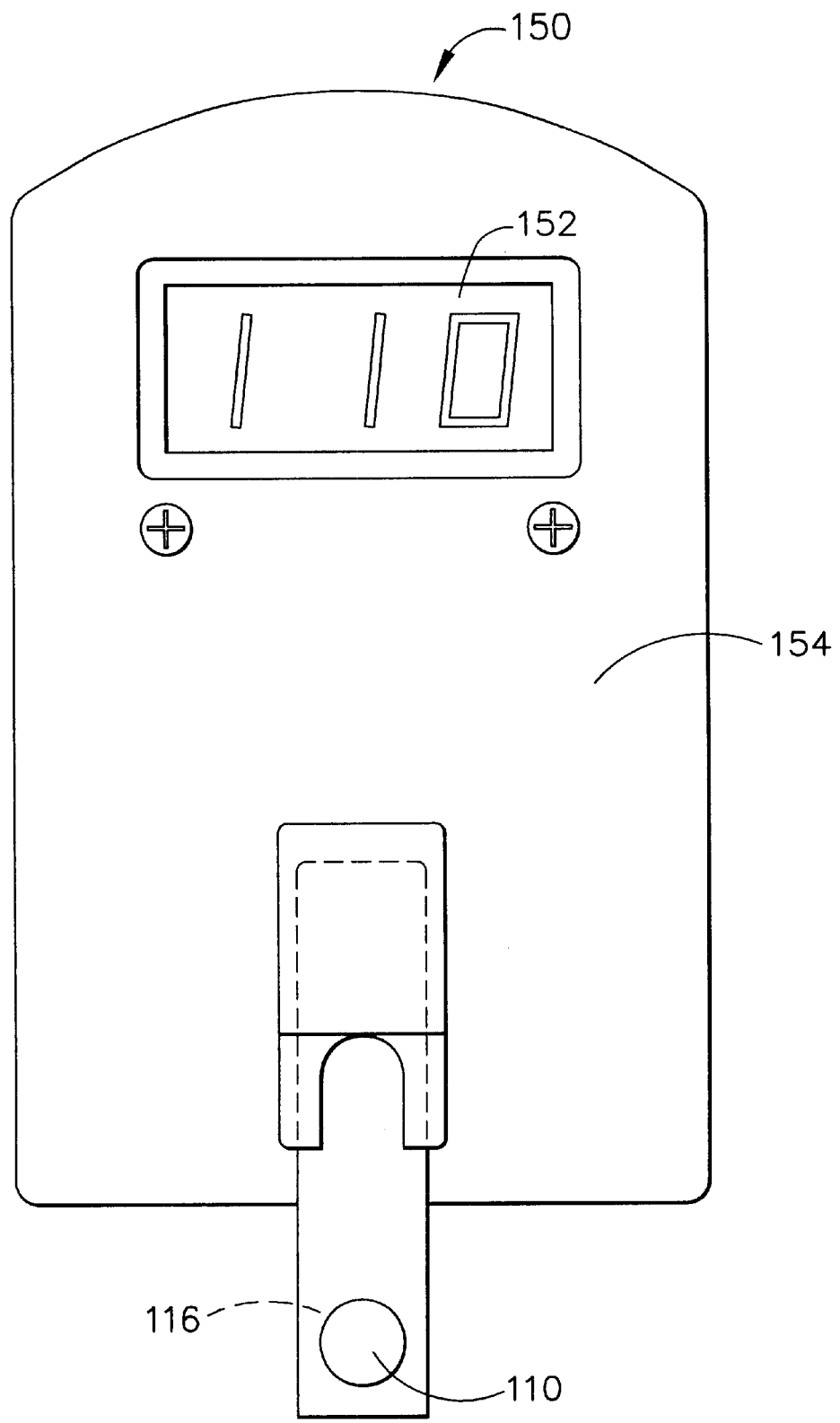
FIG. 10 is a diagrammatic view of a self-contained sensing device that includes a microneedle patch or strip, along with a display.

A self-contained sensing unit with microneedles and a pump-type diaphragm is illustrated in FIG. 10. The self-contained device is designated overall by the reference numeral 150, and has a microneedle array 110 and, on the opposite side of an extendable member 154, has a diaphragm 116 that is to be pumped by a person's finger or thumb. This self-contained unit includes a digital display 152 that provides a direct readout in engineering units of a percent concentration, or in other units as desired for a particular application.

Figure 11:
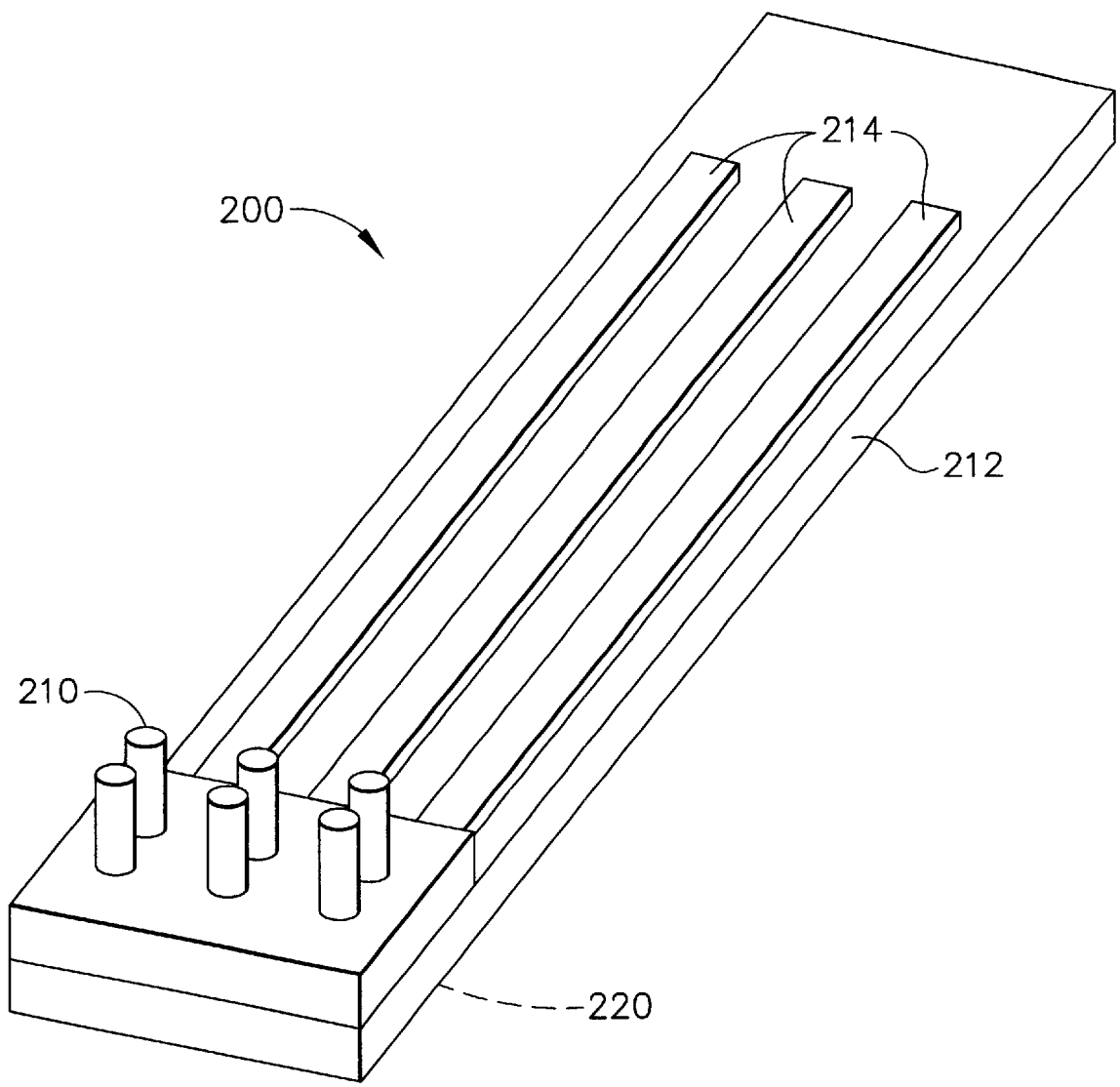
FIG. 11 is a perspective view of a microneedle strip that contains an array of solid microneedles that are coated with a compound that allows them to act as an electrochemical sensor, and a set of electrodes, as constructed according to the principles of the present invention.
Figure 12:
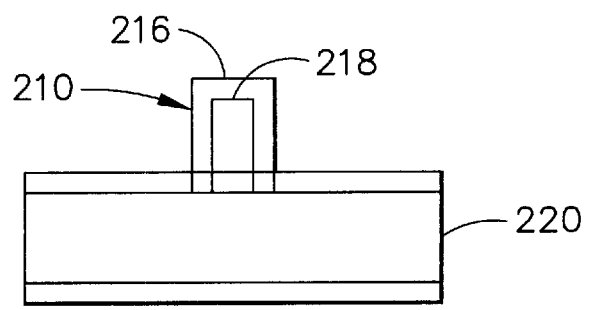
FIG. 12 is a cross-sectional elevational view of the coated microneedle strip of FIG. 11.

Another alternative embodiment for a strip-type sensor is illustrated in FIG. 11, in which the microneedle strip sensor is generally designated by the reference numeral 200. Sensor strip 200 also includes three electrodes 214 that run along a body 212 to an array of microneedles 210. In this configuration, the microneedles 210 are solid, not hollow, and contain an outer coating of a material that converts the microneedles into an electrochemical sensor. FIG. 12 illustrates a cross-section of such a microneedle, in which the microneedle 210 has a main projecting body portion at 218, which is coated with a material 216.

The material coating 216 of the solid microneedles 210 is designed to react with the concentration of the interstitial fluid of interest, and this coating is placed into contact with the electrodes 214 of the strip portion of the body 212. This electrical contact takes place at the area 220, as illustrated on FIGS. 11 and 12. By use of this construction, there is no actual withdrawing of fluid from the skin, but instead the interstitial fluid directly contacts the coated surface 216 of the microneedles 210, and causes an electrical response to the chemical concentration of interest. Since no fluid is withdrawn from the skin, this type of device is referred to as an "in-situ device."

Such coated solid microneedles 210 can be constructed in various manners. Some of these construction techniques are disclosed in two patent applications assigned to The Procter & Gamble Company, under Ser. No. 09/579,798 which was filed on May 26, 2000, and titled "Method of Manufacturing an Intracutaneous Microneedle Array," and Ser. No. 09/808,534, filed on Mar. 14, 2001, and titled, "Method of Manufacturing Microneedle Structures Using Soft Lithography and Photolithography." These other patent applications are incorporated herein by reference in its entirety.

In one embodiment, the electrodes 214 are brought to an external terminal that can be attached to an external "electron sensor" such as that described and illustrated in FIG. 9. This external sensor will receive the electrical signal from the electrodes 214 and display or otherwise indicate the concentration for the fluid of interest. Alternatively, a self-contained device could be used that includes a display of its own and a concentration analyzer detector.

Figure 13A:
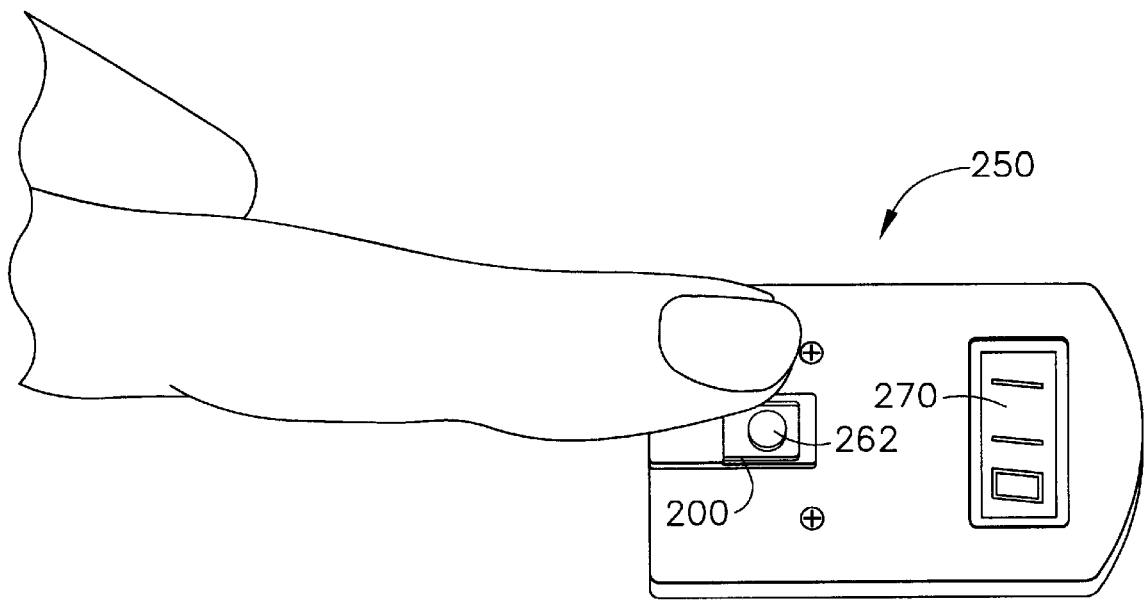
FIG. 13A is a diagrammatic view of a self-contained microneedle sensing device that can take in-situ samples through the stratum corneum of skin, and which contains a microneedle strip and a display.
Figure 13B:
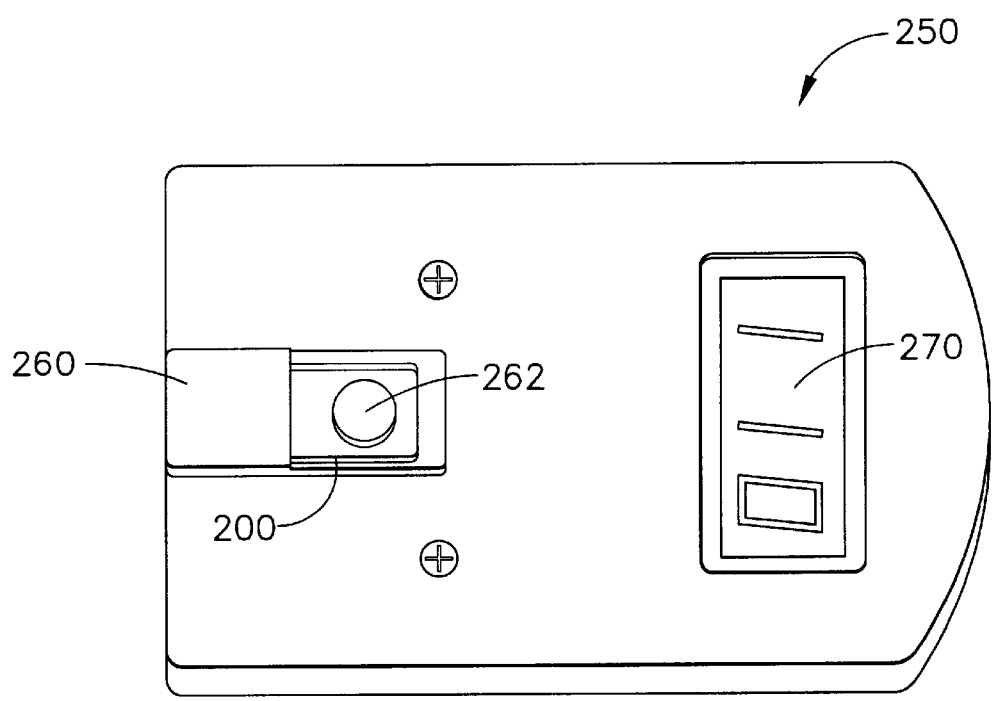
FIG. 13B is a diagrammatic view of the self-contained microneedle in-situ device of FIG. 13A.

A self-contained sensing apparatus is illustrated in FIGS. 13A and 13B as an in-situ device, and is designed as a self-contained unit that includes a display for the concentration of a fluid of interest. The overall device is designated by the reference numeral 250, and includes a replaceable sensor strip, such as the strip 200. This microneedle strip 200 is designed for a onetime use, and to be thrown away after a single use. Therefore, the strip must first be loaded onto an extending member, designated by the reference numeral 260. The microneedle array is located on this extendable member 260, and is designated at the reference numeral 262.

As shown in FIG. 13A, a person's finger is to be pressed against the microneedle array 262, and the concentration of the fluid of interest will then be measured and an electrical response generated within the electrodes (not shown on FIG. 12). Since the device 250 is self-contained, it includes its own concentration detector with a display at 270 (see FIG. 13B), which in this case is a digital display that provides a direct readout in engineering units (such as percent concentration, or mmol/dl).

The self-contained sensing apparatus 250 can be used in various modes of operation. For example, the microneedle array 262 can be pressed against skin a single time to generate a data sample that can be read by the electronics, thereby determining a concentration of a biological fluid of interest. This would be a "one-touch" application, in which the single data sample is all that is required.

Alternatively, the microneedle array 262 can be pressed into the skin for a much longer time duration, in which multiple data samples are taken by the electronics. Depending upon how many samples are desired (or can be stored in memory), and how quickly these samples are taken (i.e., the sampling time interval), such a system can effectively operate as a continuous concentration monitoring system. If the solid microneedles are used, then no biological fluids are extracted over the relatively lengthy time interval (i.e., the sampling period).

Further alternative designs are contemplated in the present invention. For example, the multiple data samples described in the previous paragraph can be used for trend analysis, if desired. Moreover, the self-contained sensing apparatus 250 can be equipped with a relatively large data storage memory capacity in situations where a large quantity of data is desired for such a trend analysis. The large memory capacity could be implemented by use of a flash memory, EPROM's, hard disk drive, or optical discs, and the like. Furthermore, a communications link could be added so as to download the data samples to a remote computer (e.g., over a network) that may have a much larger memory storage device; or the communications link could send "refined information" when desired. The term "refined information" could involve calculated values of the samples, which may involve averages, arithmetic means, maxima or minima, etc., all of which may be important to a researcher or to a patient's diagnosis. The opposite would be to send "raw data," which could consist of binary numbers output by the sensor or transducer, for example.

Figure 14:
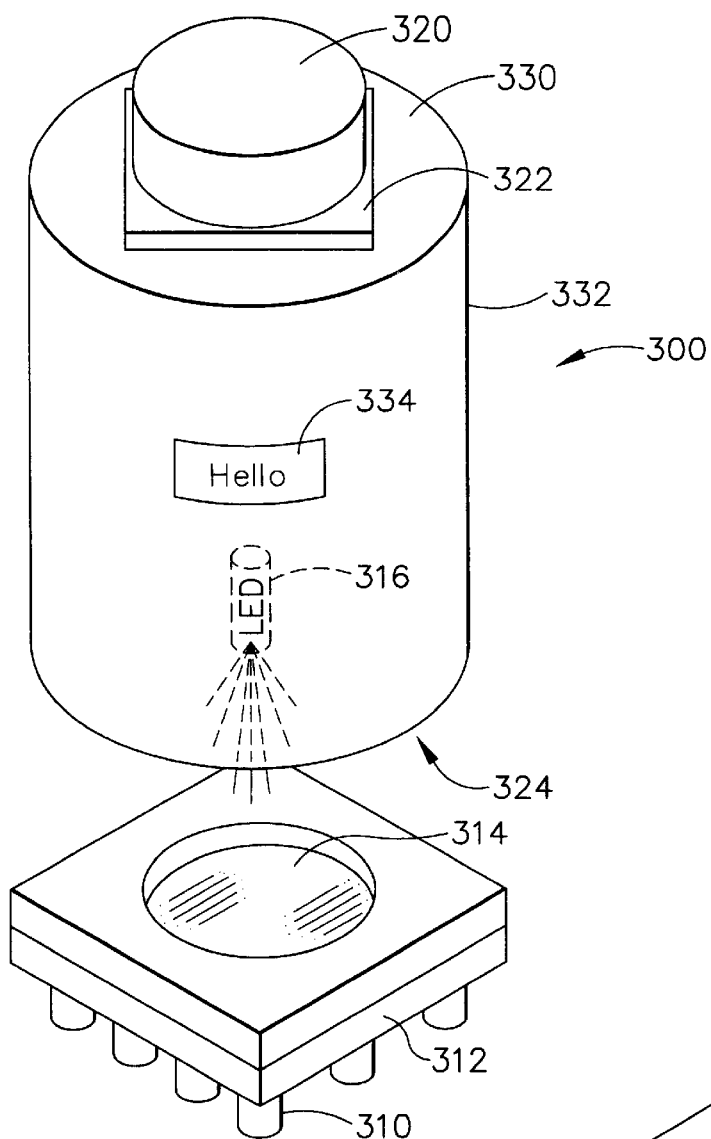
FIG. 14 is a diagrammatic perspective view of a two-part, self-contained microneedle sensor that contains an attachable/detachable array of microneedles, an optical sensor pad, a light source and a light detecting unit, a diaphragm pump, and a display device, constructed according to the principles of the present invention.

FIG. 14 illustrates a two-part optical sensing unit that uses microneedles to sample interstitial fluids of skin. The overall unit is designated by the reference numeral 300, and includes an attachable/detachable microneedle array portion with microneedles 310, a body 312 that includes a reservoir (not shown) and a diaphragm pump (not shown), and a "color interrogation window" 314. In this instance, the microneedles 310 preferably are hollow.

The sensing device 300 also comprises the main body portion which includes some type of light source 316 such as an LED (light emitting diode), an optical detector or sensor (not shown) such as a phototransistor or photodiode (or an array of such phototransistors or photodiodes), and a manually-operated control actuator 320 mounted on a top surface 320 of a housing 332 of the main body portion, which also includes a display or other type of readout at 334. The control actuator 320 preferably is a pushbutton-like device, and can be in more than one position with respect to its planar base at 322. This will be discussed in greater detail below. The main body portion 300 has an upper surface at 330, upon which the control actuator 320 is situated. When the control actuator 320 is operated by a person's hand or finger, it causes fluid to flow through the microneedles 310.

The microneedle array 310 preferably is disposable, along with the microneedle body portion 312 and its "color interrogation window" 314. Is this configuration, the entire attachable/detachable microneedle body portion 312 comprises a one-time use device. The microneedle body portion 312 is constructed so as to readily snap into place (or otherwise be affixed) at a receptacle portion 324 at the bottom (on FIG. 14) of the main body housing 332.

Figure 15:
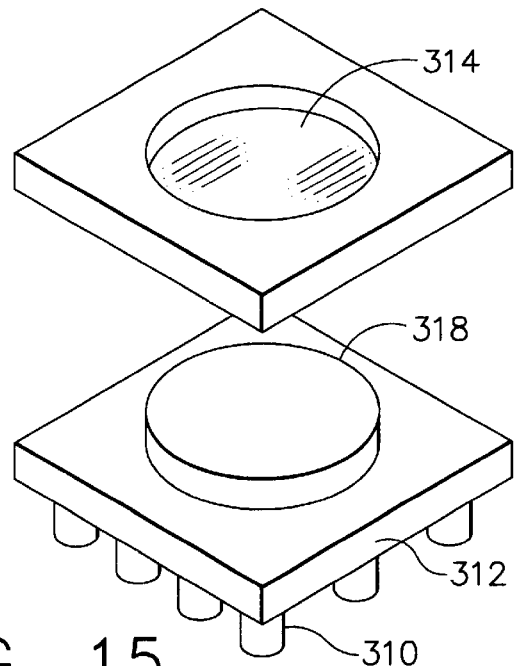
FIG. 15 is an exploded view of a portion of the self-contained microneedle sensor of FIG. 14.

FIG. 15 illustrates an optical sensor "pad" 318 that is placed above the lower body 312 and which is contacted by the interstitial fluid that is withdrawn through the microneedles 310. This optical sensor pad 318 will be of a nature that will vary its color when a varying concentration of a particular fluid comes into contact with the optical sensor pad 318. The light source 316 will shine through the window 314 onto the pad 318, and the wavelength of the reflected light from the pad will be indicative of the concentration of the interstitial fluid that has been withdrawn through the microneedle array 310. Once a sample of interstitial fluid has been taken, the microneedle body portion 312 can be disposed of, and a new one placed on the skin the next time a sample is to be taken. To prepare the sensing device for use, the main body 332 of the overall sensing unit 300 is placed on top of the body 312, over the window 314.

Figure 16:
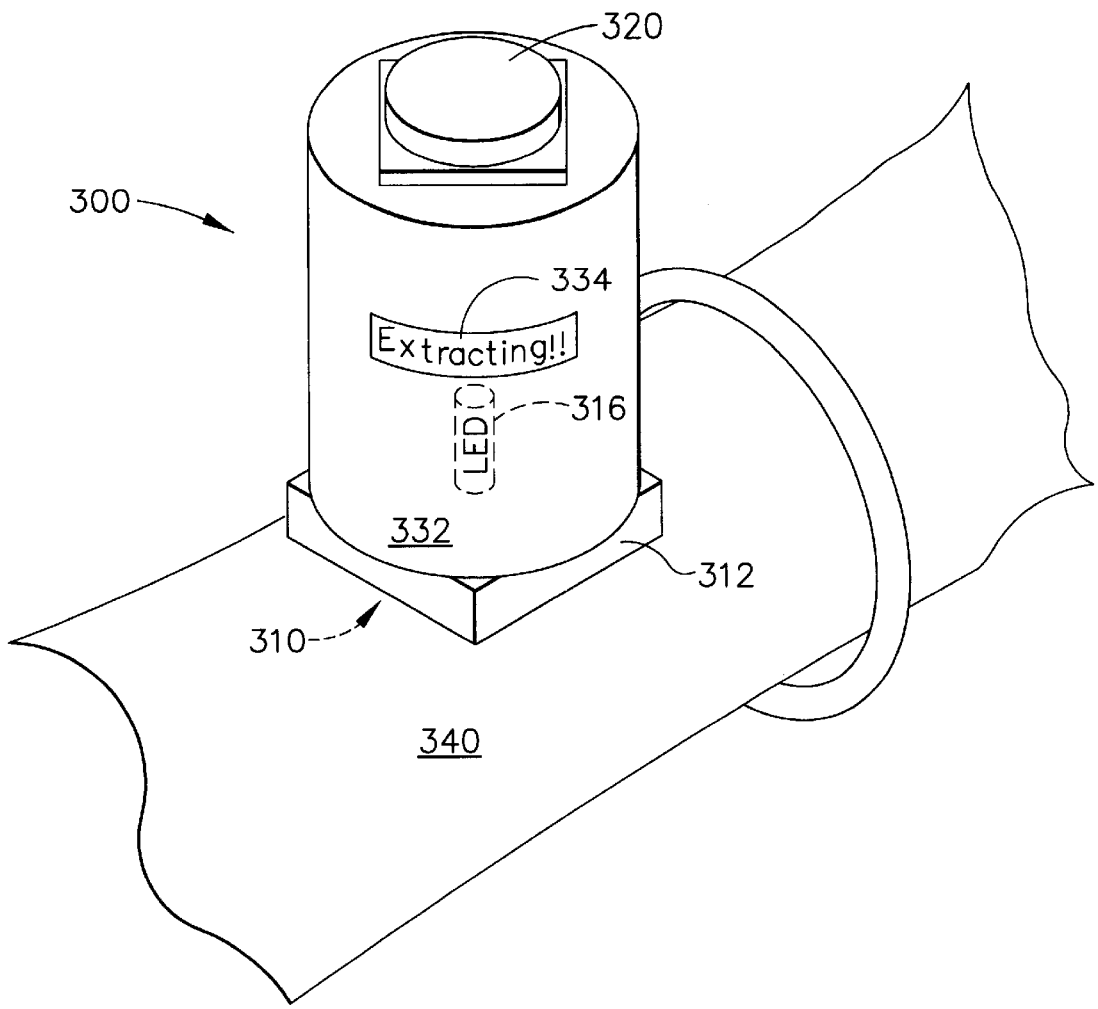
FIG. 16 is a diagrammatic view of the self-contained microneedle sensor of FIG. 14, while it is extracting fluid from a person's hand.

To use the sensing device 300, it is pressed against the skin, which forces the microneedle array 310 into the skin, for example, of a person's hand or arm 340, as illustrated in FIG. 16. Once in position, the control actuator 320 is actuated with a finger (perhaps of a different hand) and the interstitial fluid will be withdrawn through the microneedles 310 so that the LED 316 can shine upon the sensor pad 318 to have the optical detector (not shown) measure the wavelength change. The final result is displayed on an LED display or readout at 334; during the actual process of extracting the fluid, this display 334 could be configured to show the word "Extracting."

During the actual extraction process of the interstitial fluid from the person's hand or arm 340, the top pushbutton (control actuator) at 320 is pressed down (or otherwise actuated) by a finger or hand. This causes a pressure or vacuum to be exerted and, in the case of extracting interstitial fluid, causes a vacuum to occur near the microneedles to extract the fluid from the skin. Similar to the earlier-discussed embodiments, the control actuator 320 could be pressed a single time, or could be pressed several times if that is the desired methodology to obtain enough fluid. On the other hand, the control actuator pushbutton 320 could be "cocked"—or the diaphragm pump in the reservoir area could be "primed"—such that when this control actuator 320 is released from a lowered position, it will cause a vacuum to occur and thereby withdraw the interstitial fluid from the skin.

Figure 17:
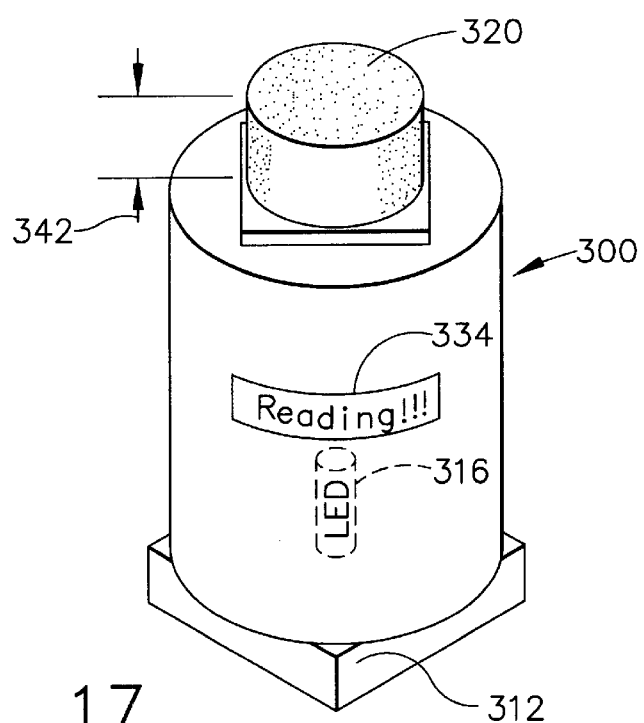
FIG. 17 is a diagrammatic view of the self-contained microneedle sensor of FIG. 14, after a fluid sample has been extracted.

FIG. 17 shows the result, in which the interstitial fluid has been withdrawn and is now within the reservoir, and can be sampled and analyzed at that time. The dimension at 342 illustrates the fact that the control actuator pushbutton 320 has been altered in its position with respect to that illustrated in FIG. 16. The dimension 342 is illustrating the distance between the top of the pushbutton 320 and the top surface 330 of the main body of the sensing device 300.

The display unit 334 could display a message such as, "Reading," and after the interstitial fluid sample has been analyzed, it could display the result in engineering units, in a message such as "101 mmol/dl."

One other advantage of the embodiment 300 illustrated in FIGS. 14–17 is that the entire sensor unit is an electronic device and the calibration can automatically be performed electronically, as needed. Another main advantage is that the microneedle portion can be made to be disposable, and can be easily placed on the skin and then have the main body 332 of the sensory unit 300 placed on top of the microneedle body 312. Alternatively, the microneedle array body 312 can be "pre-loaded" into the main body 332 of the overall sensing device 300. This entire assembly will then be placed upon the skin for having a sample extracted. Once the sample is taken, the microneedle array body 312 can be popped or clicked out of the main body 332 of the sensing device 300, and another array 312 can be pre-loaded when needed.

Another alternative embodiment for the self-contained detector/display unit 300 is to provide solid microneedles at 310 instead of hollow microneedles. In this situation, the microneedles 310 could be made of a transparent material such that the light source 316 may shine down directly through the microneedles and into the skin. The sensing device would then not be an optical sensor pad, but instead would be some type of optical coupler, such as a phototransistor or photodiode that would directly measure a change in wavelength when viewing the interstitial fluid through the transparent solid microneedles 310. Either the interstitial fluid itself would exhibit a change in wavelength or intensity due to variations in the concentration of the chemical of interest, or the transparent material would exhibit a change in wavelength or intensity due to such variations. This type of microneedle device can be constructed according to a methodology disclosed in a patent application assigned to The Procter & Gamble Company, under Ser. No. 09/579,798, filed on May 26, 2000, and titled, "Method of Manufacturing an Intracutaneous Microneedle Array." As noted above, this other patent application is incorporated herein by reference in its entirety.

Figure 18:
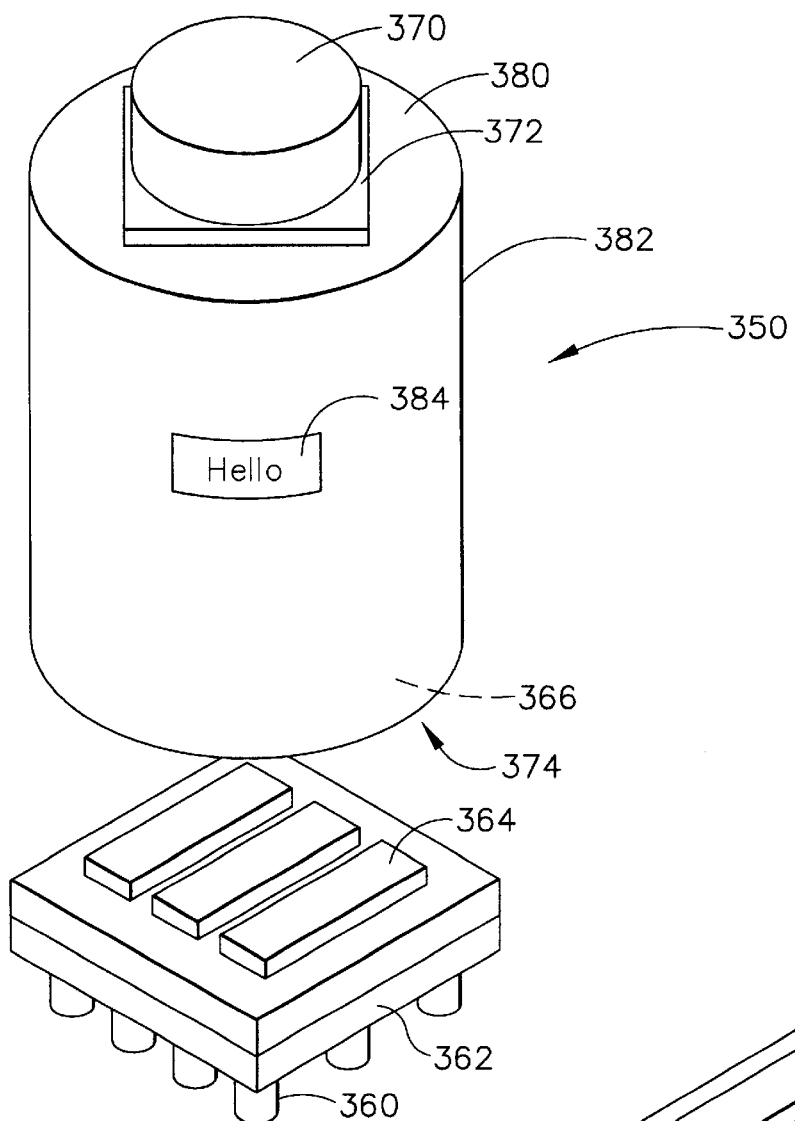
FIG. 18 is a diagrammatic perspective view of a two-part, self-contained microneedle sensor that includes an attachable/detachable microneedle array, a set of electrodes, an electrosensor pad, an electronic interface device, a diaphragm pump, and a display, constructed according to the principles of the present invention.
Figure 19:
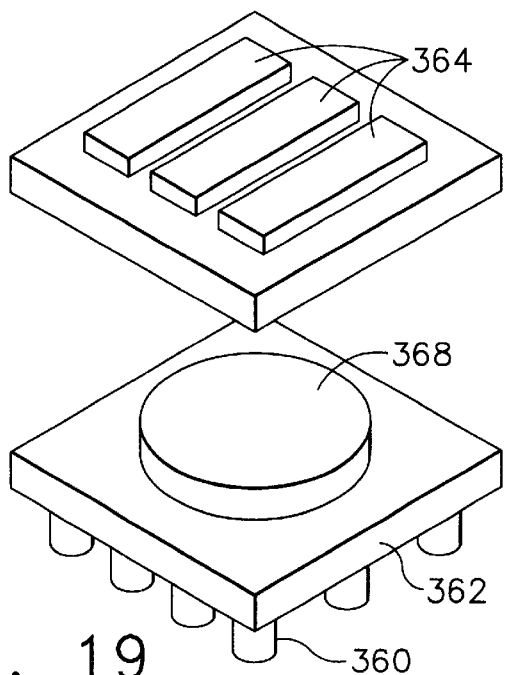
FIG. 19 is an exploded view of a portion of the self-contained microneedle sensor of FIG. 18.

FIG. 18 illustrates another two-part self-contained fluid extracting and sampling device, generally designated by the reference numeral 350, that uses attachable/detachable microneedles, and includes some type of display unit. This device 350 also includes a disposable microneedle array unit 362, which includes the microneedles 360, and three electrodes at 364. A receptacle or receiving portion 374 is also included near the bottom portion of the overall device 350 to attach to, or snap together with, the disposable microneedle array unit 362.

The top portion of the self-contained sensor 350 includes a wall structure at 382, and a display device at 384. This top portion 382 also includes a thumb or finger-operated pushbutton 370 that actuates a diaphragm or pump device within the disposable microneedle array unit or body 362. This pushbutton actuator 370 is placed on top of a substantially planar substrate or surface 372, and the entire top button unit is positioned on top of the upper surface 380 of the main body 382 of the top portion of the sensing device 350. The top portion main body 382 also includes some type of electrical interfacing circuit 366 that will receive an electrical signal from the electrodes 364 of the disposable microneedle array unit 362.

The top pushbutton 370 will operate much as the top pushbutton 320 of the previously described embodiment 300 illustrated in FIGS. 14–17. The microneedle portion 362 includes the microneedle array 360 and an "electro-sensor pad" 368 that is placed beneath the three electrodes 364, and which makes contact with those electrodes 364. The electrosensor pad 368 acts as an electrochemical sensor, and causes an electrical charge or low voltage to be induced into the electrodes 364. As a fluid concentration of interest varies, then so will the electrical output signal that is produced by the electrodes. This in turn will be detected by the interface electronics in the main body portion of the sensor 350.

The microneedles themselves would typically be hollow, although they could be solid if an outer coating is placed on the solid microneedles that reacts to the interstitial fluid. Such solid, coated microneedles will create an electrical contact with the electrodes 364 that will produce an electrical response based upon the concentration of the fluid of interest within the interstitial fluid.

Figure 20:
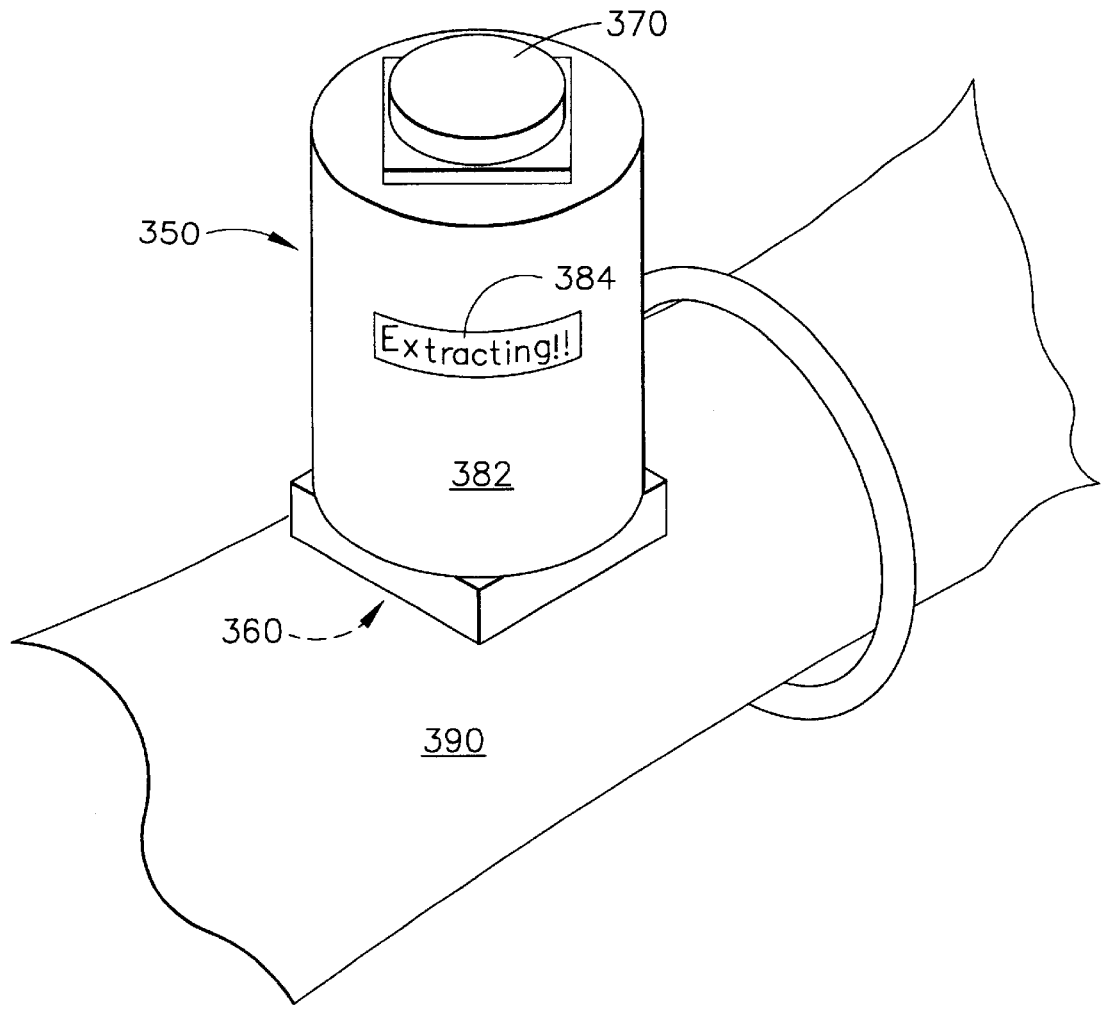
FIG. 20 is a diagrammatic view of the self-contained microneedle sensor of FIG. 18, while in an extracting mode as it is placed on a person's hand.

FIG. 20 shows the sensing device 350 while in use, in which the microneedle array body 362 is pre-loaded into the bottom of the top portion 382, and the entire device 350 is then placed on the hand or arm 390 of a person. At that time, the top button is depressed at 370, and the fluid is extracted (in the case of hollow microneedles) or the fluid is sensed (in the case of solid microneedles with a particular coating). The display 384 could now show a message such as, "Extracting."

Figure 21:
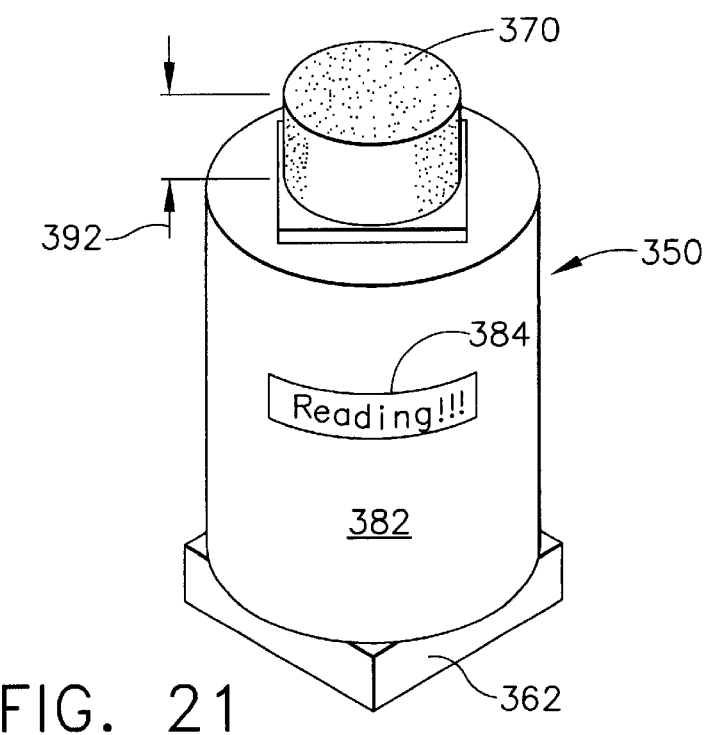
FIG. 21 is a diagrammatic view of the self-contained microneedle sensor of FIG. 18, after a sample has been extracted.

FIG. 21 illustrates the sensing device 350 after the fluid sample has been taken, and the fluid is within the reservoir of the microneedle body 362. In FIG. 21, the top pushbutton 370 has been re-positioned, as seen by the dimension 392 in which the top button now extends further than in the illustration of FIG. 20. A message on the display unit 384 could now say "Reading," during which time the microneedle body 362 is still attached to the top portion 382. Finally, once the analysis has taken place, the display unit 384 can provide a different message, which preferably would be the actual concentration of the fluid of interest, either in percent or in some type of engineering units. For example, the display could provide a message such as, "101 mmol/dl."

Figure 22:
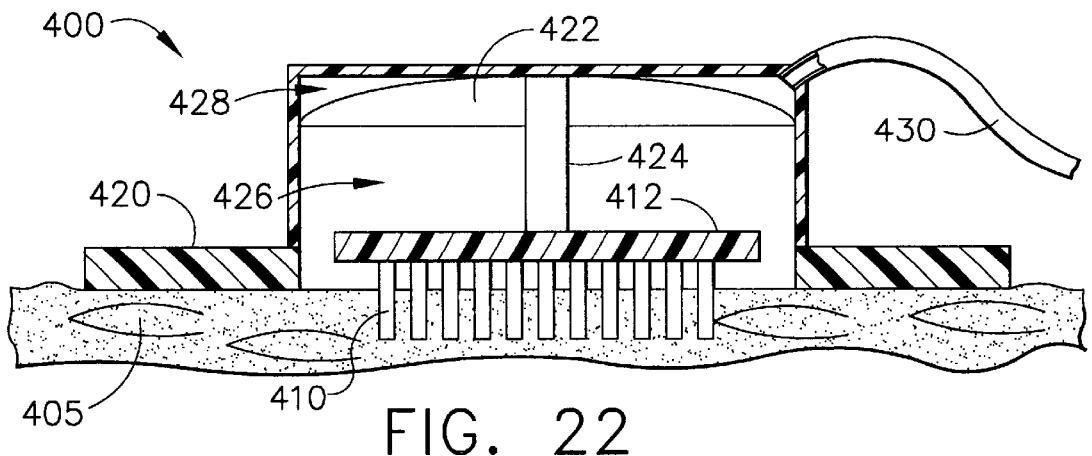
FIG. 22 is a cross-section view of a microneedle extracting device that illustrates a microneedle array while it is in position on the skin and while piercing the stratum corneum of the skin, constructed according to the principles of the present invention.

FIG. 22 illustrates a continuous measurement system using microneedles that can be placed on skin, then later have individual fluid samples taken by the mere pressing of a button, and later have the sensing unit dispose of the sample while potentially remaining in place on the skin for later samples to be taken. The microneedles themselves can remain in place on the skin while later fluid samples are extracted, either at predetermined time intervals, or as needed. Alternatively, the microneedles could be withdrawn from the skin, but then later re-inserted at predetermined time intervals, or as needed.

In FIG. 22, the overall structure 400 is placed upon the skin 405. the microneedle array 410 is pressed into the skin, preferably through the stratum corneum. This is accomplished by pressing on top of the unit 400 at a plunger 424 that is in communication with a membrane or diaphragm at 422. The microneedle array 410 includes a substrate or base at 412.

In this position, the volumetric space at 426 may have some interstitial fluid within its confines, although there is no particular pressure or vacuum being exerted at this time. The volumetric space at 428 also may contain some interstitial fluid but, again, there is no particular pressure or vacuum being exerted at this time. The volumetric spaces 426 and 428 are both variable-volume chambers, in that the diaphragm/membrane 422 is flexible and thereby causes these spaces 426 and 428 to effectively change size and shape.

A tube at 430 is brought into hydraulic communication with the top volumetric space at 428. As used herein, the term "hydraulic communication" refers to any type of apparatus that allows a transfer or flow of fluid to occur between one structure and another; the word "hydraulic" does not imply that high pressures are involved, and it is not necessarily restricted to liquids (both gas and liquid can be referred to as being fluids). In other words, "hydraulic communication" is equivalent to "fluidic communication."

Figure 23:
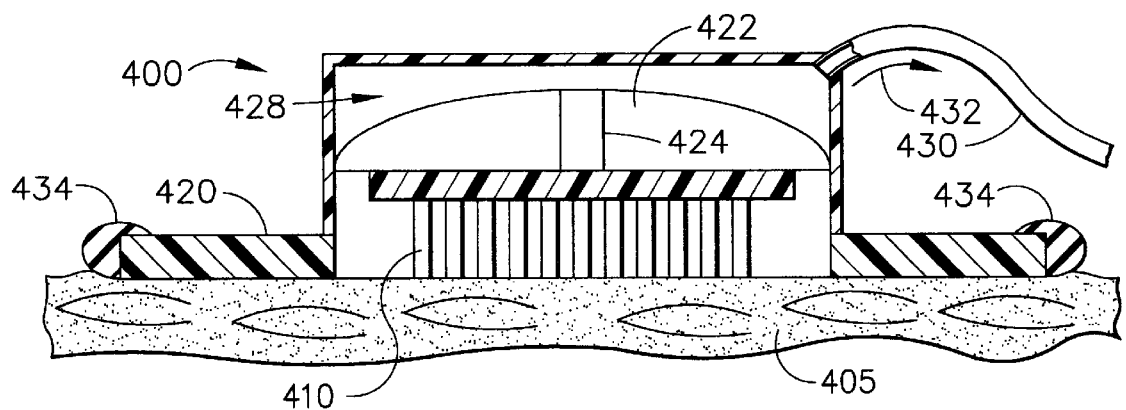
FIG. 23 is the microneedle array structure of FIG. 22 in which the microneedle array has been withdrawn from the stratum corneum, and fluid has been extracted.

FIG. 23 illustrates the microneedle array 410 having been withdrawn from the main stratum corneum layer of the skin 405, which occurs when the diaphragm or membrane 422 is released. This causes interstitial fluid that was extracted from the epidermis to be placed into the volumetric space 428, which also causes the extracted interstitial fluid to be sent into the tube 430. The fluid is directed down the tube 430 in the direction depicted by the arrow 432. The base of the overall unit 400 is illustrated at 420 as extending along the sides of the microneedle array and volumetric space portions, and this planar base 420 extends along the skin surface. This area of the skin is occluded, which can be accomplished by adhesive tape or some other type of occluding compound 434. In this manner, the area beneath the microneedle array is sealed off from the exterior portions of the environment, which permits pressure or vacuum to be applied.

In FIG. 22, the top button/plunger 424 was depressed, which deformed the diaphragm/membrane at 422 and displaced the microneedle array 410 into the skin 405. In FIG. 23, the opposite occurs because the top button/plunger 424 is released, and the diaphragm/membrane 422 has its shape deformed so as to withdraw fluid into the chamber at 428. This fluid is now accessible to be pumped to an external sensor along the tube 430.

After a particular sample of interstitial fluid is taken and analyzed, then it can be disposed of by the external sensor (not shown on FIGS. 22 and 23). Later, either as needed or at predetermined time intervals, further samples of interstitial fluid can be acquired by pumping them from the chamber 428. This is achieved by one of two methods: (1) further piercing the skin with the microneedle array by depressing the plunger at 424, which would have the appearance of that of FIG. 22; or (2) allowing the microneedles array 410 to remain above the skin surface (as viewed in FIG. 23), and depend upon fluid to continue to seep out through the holes originally formed in the stratum corneum by the initial depression of the microneedles into the skin. In this situation, the interstitial fluid at 428 will continuously exhibit the concentration levels of whatever compounds or fluids that will be of interest, and this fluid within chamber 428 can be periodically pumped through the tube 430 to an external sensor.

Figure 24:
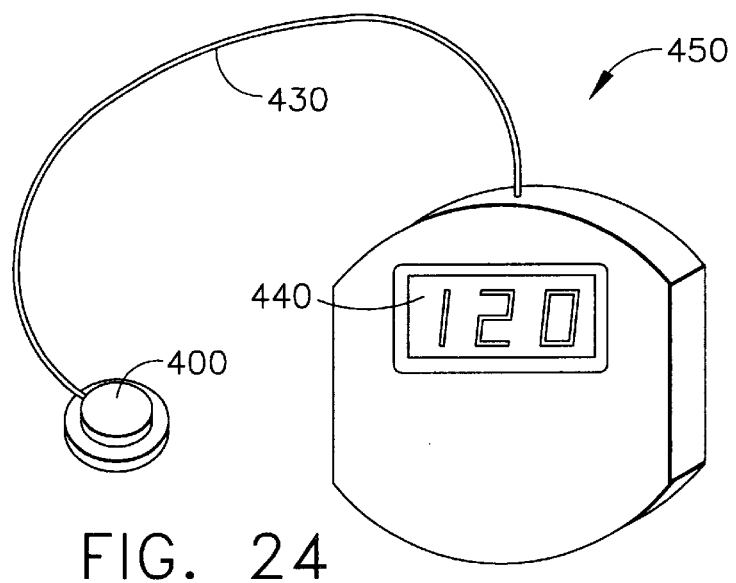
FIG. 24 is a diagrammatic view of a self-contained microneedle sensor that interfaces to the microneedle array of FIG. 22.

FIG. 24 illustrates an external sensor at 450, and it can be seen that the microneedle array structure 400 is attached to flexible tube 430, which runs back to the detecting device 450. The sensing system 450 preferably will contain a display, such as that illustrated at 440. The display 440 can display appropriate messages, such as "Extracting," or "Reading," or the actual engineering units of the final result of the fluid concentration.

An alternative embodiment to the system illustrated in FIGS. 22–24 would be to use solid microneedles that have an outer coating that will provide an electrical signal to an electrochemical sensor, and output an electrical signal along a set of wires to the display unit instead of providing fluid through a tube such as the tube 430. If using solid microneedles, then it would be important to either leave the microneedles within the stratum corneum during the continuous period within which samples are to be taken periodically, or to re-insert the solid microneedles into the stratum corneum at the time of the actual samples to be taken.

Figure 25:
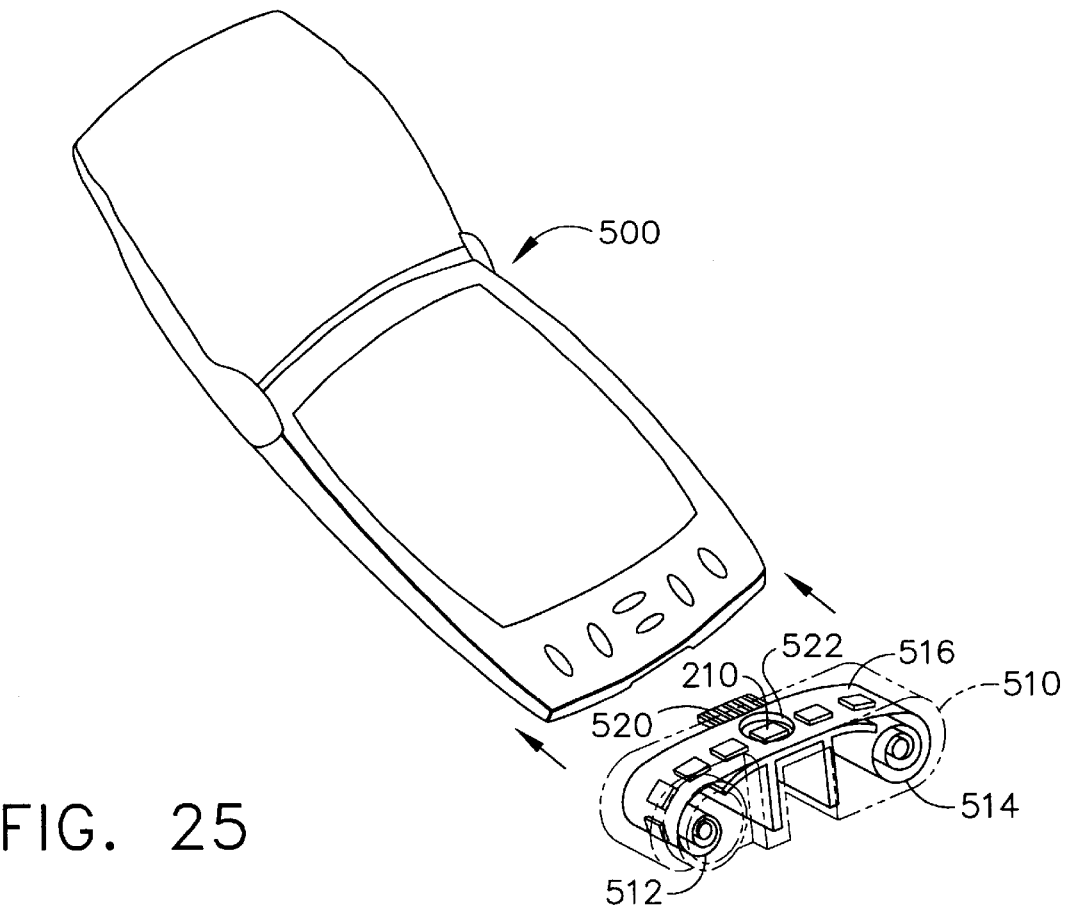
FIG. 25 is a diagrammatic view of a strip of microneedles in a plug-in cartridge that can interface to a PDA device, such as a palm pilot, as according to the principles of the present invention.

FIG. 25 illustrates an embodiment that uses a personal data assistant (PDA) such as a palm pilot, generally designated by the reference numeral 500. A plug-in cartridge 510 contains a reel of microneedle strips, in which an individual microneedle patch or array at 210 is allowed to protrude into an open area or hole at 522. Two circular reels are utilized at 512 and 514, in which 512 could be the "source reel" and the reel 514 could be the "take-up reel." A web or tape at 516 contains individual strips of the microneedles at predetermined intervals, and after the first microneedle patch or array at 210 is used, the take-up reel and source reel both rotate to advance or "index" the web or tape 516 a predetermined amount until the next unused microneedle strip or patch is positioned at the hole 522. In other words, the web or tape 516 is indexable (or indexed) to a "next" position by rotating the take-up reel 514 and source reel 512, which correctly positions the "next" unused microneedle strip/patch at hole 522.

The web or tape 516 is depicted on FIG. 25 as having a source reel and take-up reel configuration, much like a film cartridge used in a 35 mm camera, for example. Alternatively, the web/tape 516 could have a closed loop configuration, or perhaps a folded configuration, consisting of "Z"-like folds, similar to an accordion.

The plug-in unit 510 utilizes electrical connectors at 520, and this device 510 is to act as any other type of replaceable or insertable cartridge that can interface to the palm pilot 500. Driver software would typically be installed in advance on the PDA 500, which would recognize the electrical signals being transmitted from the plug-in cartridge 510 and appropriately display messages. Such messages could include "extracting," "reading," or the concentration levels in engineering units or in percent.

The plug-in sampling unit will include multiple microneedle arrays that would preferably be solid microneedles having an outer coating that will act as an electrical connector and electrochemical sensor. The sampling unit 510 would also include some type of signal transducer, such as a set of electrodes, that will produce an appropriate signal from the electrochemical sensor; additionally, an electron sensor could be included, which will produce an appropriate signal from the electrodes. The plug-in unit 510 would typically contain some type of microprocessor with an analog-to-digital (A/D) converter. In addition, some memory would typically be mated with the microprocessor, which could include random access memory (RAM) if desired, and would certainly contain read only memory (ROM), which could be on board the microprocessor if that is the type of microprocessor utilized (sometimes called a microcomputer).

As an alternative embodiment, the sampling unit 510 could include an optical coupler as the signal transducer in the microneedles extract some interstitial fluid that can be inspected by an optical sensor pad.

An output channel would be used to transmit appropriate signals through the connector 520 into the PDA 500. Typically, the output channel would transmit binary numbers or other types of serial messages to the PDA.

It will be understood that the microneedle arrays or patches 210 could contain hollow microneedles rather than solid microneedles, and in that instance a separate electrochemical sensor would likely be utilized to bring the signal to a set of electrodes that could be common for the entire plug-in cartridge 510. Alternatively, the microneedle strip 200 could include a separate set of electrodes for each one of the microneedle arrays. Ultimately, the sensing signal would go to the A/D converter and through the microprocessor before being sent to the PDA 500. In the circumstance where an individual set of electrodes is provided for each microneedle array, then the "microneedle strip" 200 would include a microneedle array (at 210), a set of electrodes, and an electrochemical sensor.

Another alternative embodiment could utilize an interfacing device other than a pure electrical connector to transfer a signal from the cartridge 510 to the main body 500 of the PDA. For example, the signal being transferred may not be a purely electrical signal. Instead, this tranferring signal could be an acoustic signal, a magnetic signal, or an electromagnetic signal. In the case of an electromagnetic signal, the wavelength used could be in the radio-frequency range, or it could be a much higher frequency so as to render the electromagnetic signal into an optical signal, or a microwave signal. In the case of an acoustic signal, its frequency could be in the ultrasonic range, so as to render it indiscernible to human ears. The transmitter and receiver units would appropriately be optical, microwave, radio, magnetic, or acoustic in nature.

Figure 26:
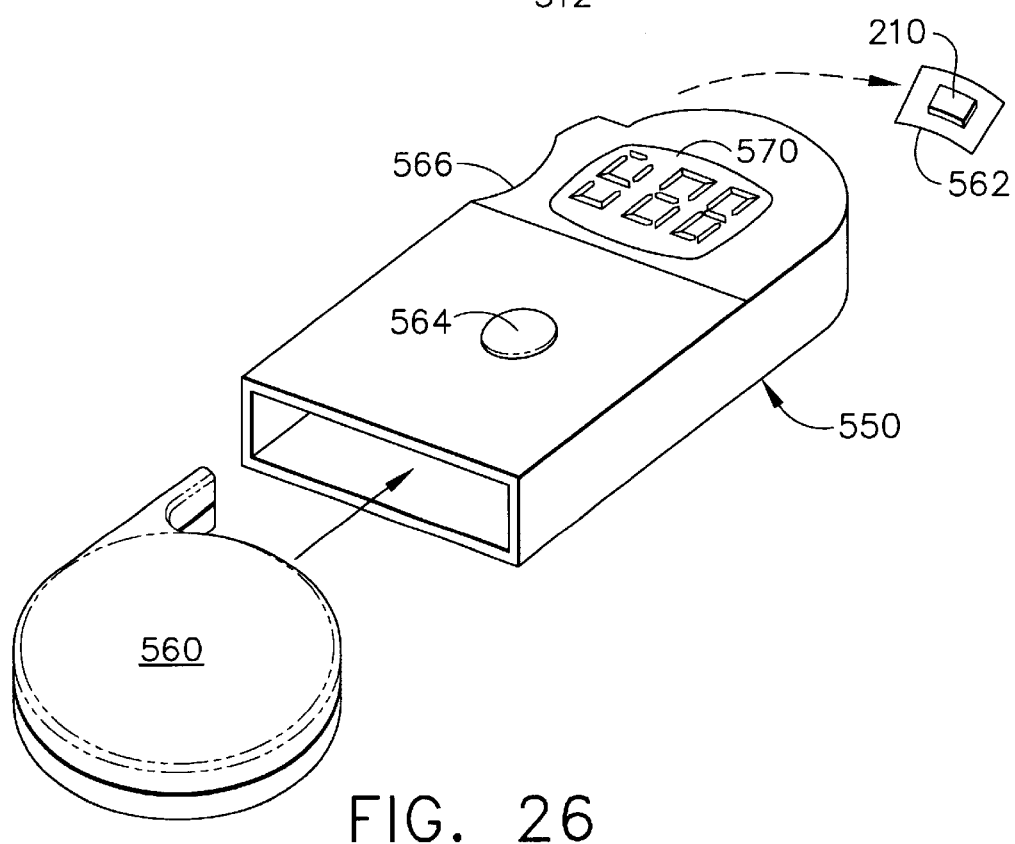
FIG. 26 is a self-contained microneedle sensor that includes a refill cartridge of microneedle strips that can extract fluids through skin, and includes interface electronics and a display, as according to the principles of the present invention.

FIG. 26 illustrates a self-contained display and sensing unit, generally designated by the reference numeral 550. This unit 550 has a refill cartridge 560 that contains multiple microneedle patches. The refill cartridge 560 can snap into the bottom of the overall device 550, and this could be used to produce a microneedle array or patch 210 (as part of a microneedle strip 200) at an opening 566 in the casing of the unit 550.

A person could place a finger or thumb against the microneedle strip 510 through the opening 566, and then actuate a pushbutton switch at 564 to cause the device 550 to extract a fluid sample, or to examine a sample using solid microneedles that will analyze the concentration of a particular compound within the interstitial fluid of the finger or thumb that is placed into contact with the microneedle array or patch 210. Once the measurement has been taken, then the spent patch or strip is ejected through an opening in the case of the device 550; the spent patch/strip is illustrated at 562.

The overall device 550 includes detecting and interfacing electronics, and a display 570 that can be used to produce a message, including the concentration of a particular compound within the interstitial fluid. This self-contained device 550 would act in a similar manner to the PDA device 500, except the self-contained unit 550 would be for a specific purpose only. Moreover, the refill cartridge 560 could contain many more microneedle strips than the take-up reel-type cartridge 510 of FIG. 25. For example, the refill cartridge 560 could have at least one hundred microneedle strips 200, while the "strip cartridge" 510 of FIG. 25 may have as few as only twenty microneedle strips 200 (each having a microneedle patch or array 210).

Figure 27:
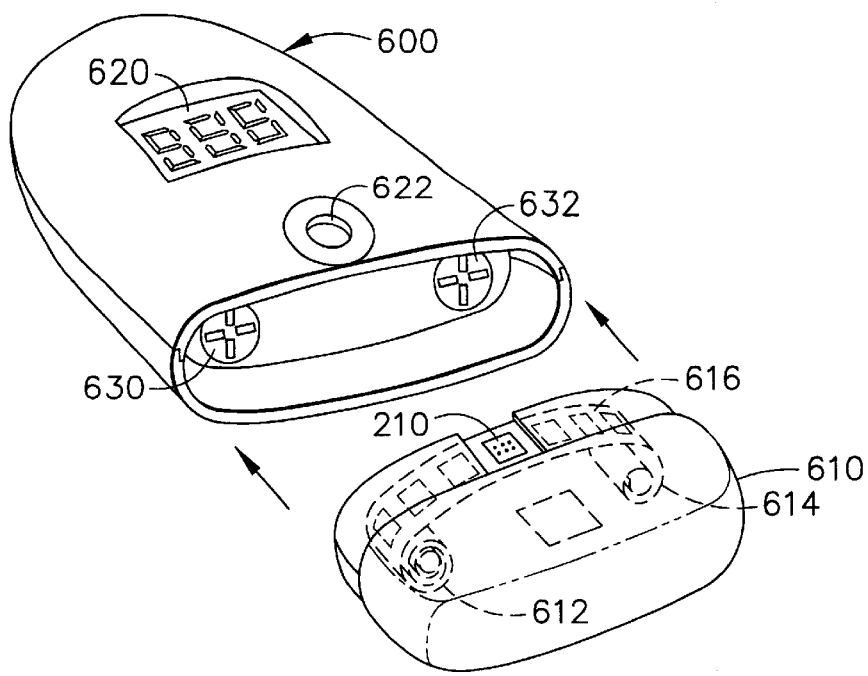
FIG. 27 is another self-contained microneedle sensing unit that includes a disposable refill cartridge that can be plugged into the interface electronics of the device, which includes a display, as according to the principles of the present invention.

FIG. 27 illustrates another embodiment of a self-contained sensor and display, generally designated by the reference numeral 600. The unit 600 includes a display 620, an opening 622 in its case, and a pair of actuating wheels at 630 and 632.

A disposable refill cartridge generally designated by the reference numeral 610 is snapped into position in the bottom of the case of the overall unit 600. This refill cartridge will contain a web or tape of microneedle strips 200 (with patches or microneedle arrays 210), and will include a source reel 612 and a take-up reel 614. The web or tape is illustrated at 616.

The drive wheels 630 and 632 are used to actuate the source reel 612 and take-up reel 614. This unit 600 will act in a similar manner to the self-contained unit 550 illustrated in FIG. 26, or the PDA-type device 500 that uses a replaceable cartridge 510, illustrated on FIG. 25.

Figure 28:
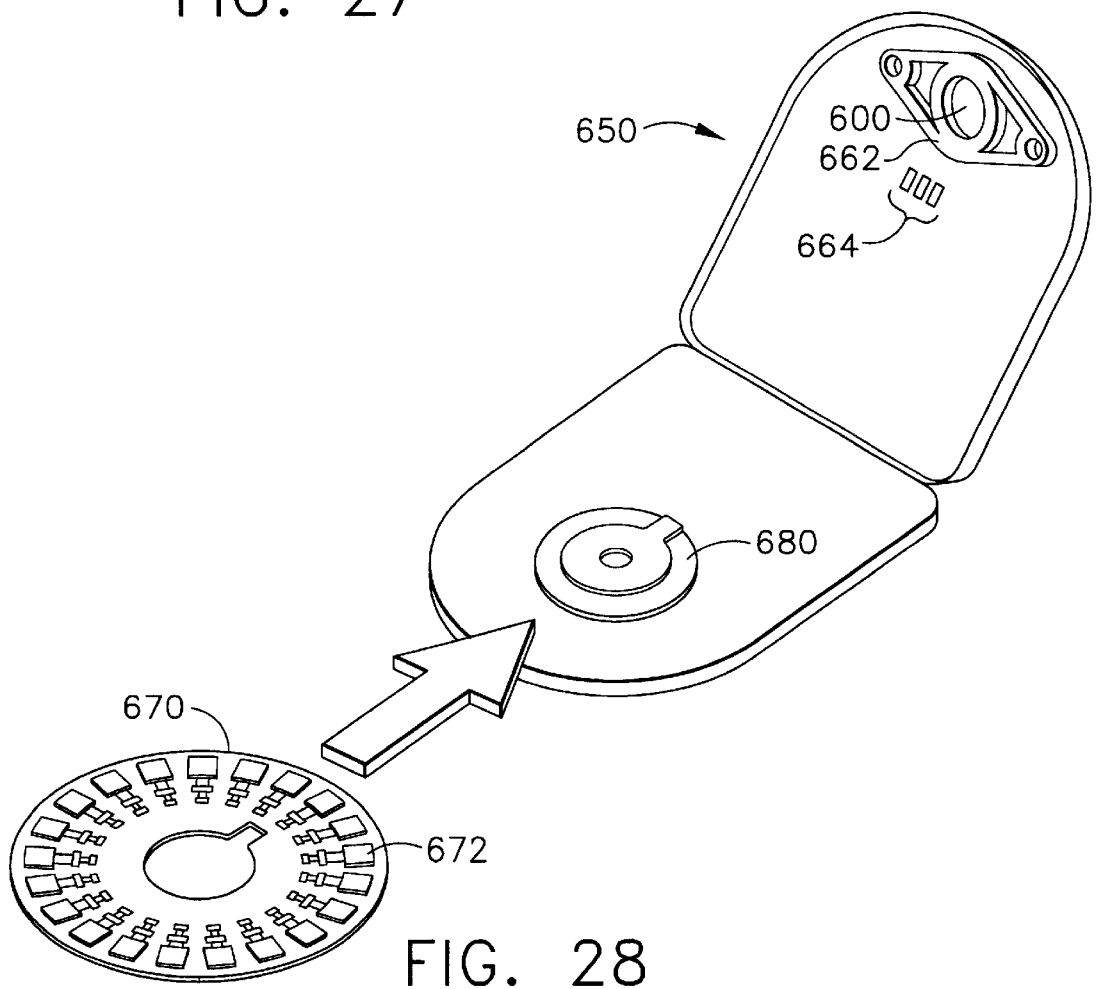
FIG. 28 is a diagrammatic view of a self-contained microneedle sensor that includes a disposable disk containing microneedle patches, which interfaces with electronics including a display, as according to the principles of the present invention.

Another alternative embodiment is illustrated in FIG. 28, in which a disk cartridge 670 is used to provide patches of microneedles to a self-contained unit, generally designated by the reference numeral 650. The disk 670 contains multiple patches 672 of microneedles, which could be either hollow or solid microneedles. The solid microneedles are preferable in situations where space is a premium and fluids are preferably not handled directly into the patches themselves.

The casing of the self-contained unit 650 can be opened along a hinge, and the top portion is flipped open to change the disk 670. The disk is placed on top of a drive wheel 680, as seen in FIG. 28. After a complete revolution of the disk 670, the self-contained unit 650 alerts the user that it is time to change the disk. Again, the microneedle patches 672 are disposable when using this device.

The top or lid portion of the case includes a finger hole 660, a finger guide 662, and electrical contacts at 664. A display (not shown) preferably is located on the exterior surface of the top or lid portion of the device 650. This display can produce messages such as "Extracting," "Reading," or numeric data in engineering units or in percentage that depicts the concentration of a fluid of interest.

It will be understood that the structural shapes disclosed in the drawings, and materials described, could be varied without departing from the principles of the present invention. Certainly the sizes of the microneedles arrays could be virtually of any usable dimensions to either withdraw interstitial fluid, or to sample such fluids in situ using coated or transparent microneedles. The signal conditioning elements and processing circuits could be of almost any conventional design that is appropriate for the transducer output signals that are produced.

Referring now to FIG. 29, a microneedle strip-type sensor generally designated by the reference numeral 202 is illustrated, which is very similar to the microneedle strip sensor 200 illustrated in FIG. 11. Sensor strip 202 includes three electrodes 214 that run along a body 212 to an array of microneedles 210. The microneedles 210 could be either solid or hollow, as desired for a particular use.

Sensor strip 202 also includes a pair of electrical conductors 532 that each have a terminal pad at 530. When electrical power is applied to the terminal pads 530, an electrical current will run along the conductors 532 and through a conductive pattern 536 at the base of the microneedles 210. When a sufficient amount of power is applied to this circuit, then the conductive pattern 536 will rise in temperature, and thereby melt at least a portion of the microneedles 210. This effectively destroys the initial shape and size of these microneedles, and they will not again be usable. The microneedles can thus be sold as a "single-use" disposable product.

The result is illustrated in FIG. 30. The microneedles have now been melted down to a much shorter length, and in this condition are referred to by the reference numeral 534. It is not absolutely necessary for the microneedles to be completely eliminated by the melting action; instead it is sufficient for the microneedles to be shortened or deformed such that they cannot penetrate through the stratum corneum of skin. Therefore, if the microneedles retain their overall shape, but are merely shortened to the point where their tips would not penetrate through the entire thickness of the stratum corneum, then they become virtually useless. Alternatively, if they retain their overall length, but have their tips deformed, or their side walls lose their shape, such that they cannot pierce the stratum corneum, then that altered condition is also sufficient to prevent their use.

The main purpose of effectively destroying the microneedles 210, by modifying their condition so as to be essentially non-usable, is to prevent their re-use. In this manner, the microneedles are limited to a one-time use, or one-time application—then they effectively self-destruct. This reduces the risk of accidental repeated insertion.

Figure 31:
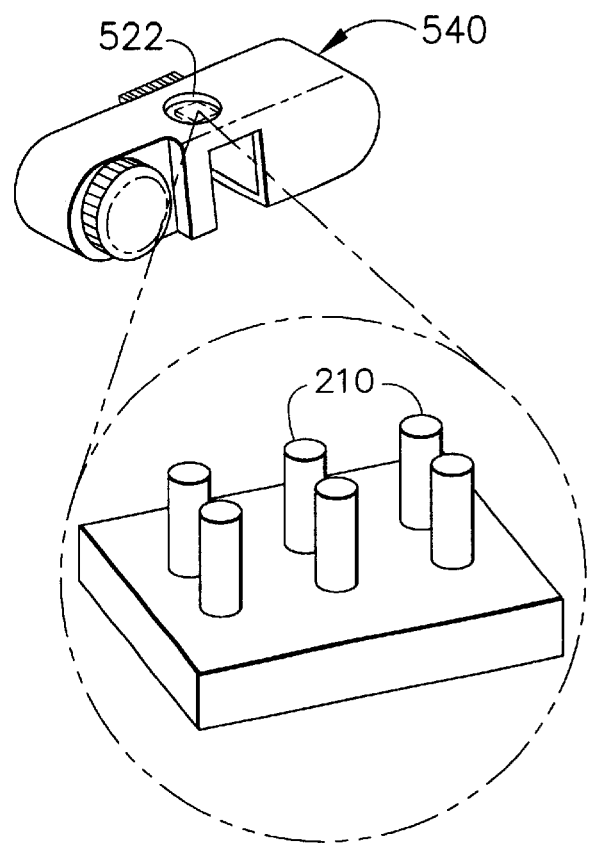
FIG. 31 is a perspective view, partially magnified, of a cartridge containing multiple microneedle patches, which also contains a mechanical device that automatically destroys or deforms the microneedles after a single use by a user, as constructed according to the principles of the present invention.

One mechanism for limiting microneedles to a one-time use is illustrated in FIG. 31. A plug-in cartridge 540 (similar to the cartridge 510 illustrated in FIG. 25) contains a reel of microneedle strips 200, each containing a microneedle patch or array 210. After the user accesses one of the microneedle patches 210, the internal tape/web 516 of microneedle strips will advance or index such that the just-used patch 210 advances past the "window" or opening 522. When this occurs, the microneedle structures are destroyed, either by heating or by a mechanical action. For example, FIG. 32 illustrates a mechanical crushing mechanism.

Figure 32:
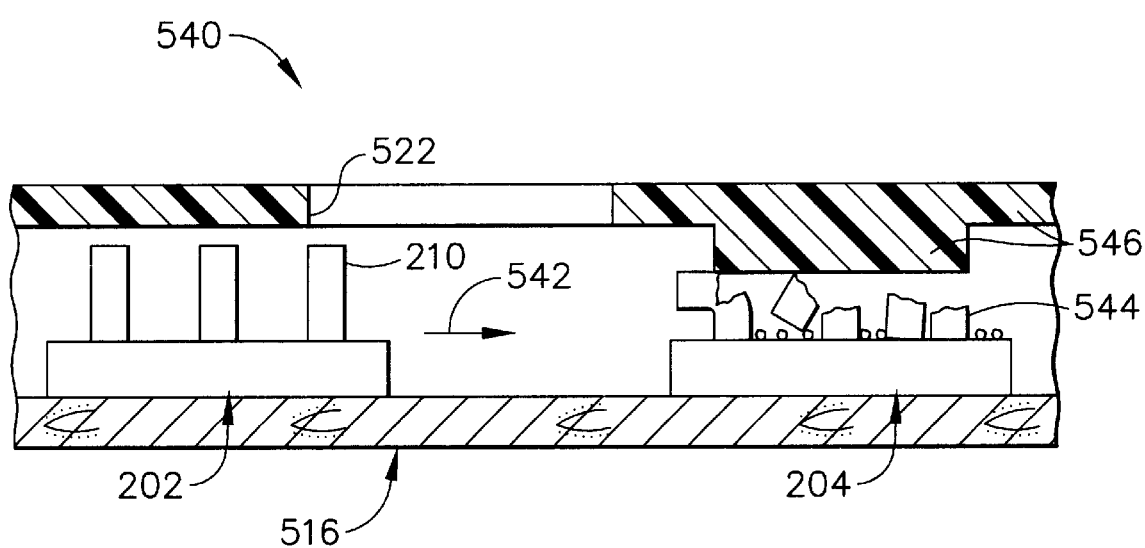
FIG. 32 is an elevational view in cross-section of a portion of the cartridge of FIG. 31, illustrating the mechanical device that destroys or deforms the microneedles, such that the microneedles cannot be re-used.

In FIG. 32, the microneedle patches/arrays are depicted at the reference numerals 202 and 204. The patch/array 202 is still intact, as its microneedles 210 have not been modified, and also have not yet been used on skin. As can be seen in the drawing, the patch/array 202 is to the left (in this view) of the opening 522, and is advancing along the tape/web 516 toward the right (in this view) as per the direction arrow 542 in order to index to a position beneath opening 522. On the other hand, the patch/array 204, which is to the right (in this view) of the opening 522, has already advanced past that opening 522, and is in the process of being destroyed or otherwise made non-reusable.

The patch/array 204 is being partially crushed in FIG. 32 by a mechanical shear-force exerting structure 546, which is a protrusion that extends down from the upper portion of the housing of the cartridge 540. When the microneedles are moved into contact with this protrusion 546, they are broken and thereby shortened, as depicted by the reference numeral 544. This shortening of the microneedles renders them inoperative for any type of re-use, thus preventing them from again penetrating the stratum corneum of skin.

As discussed above, the protrusion 546 does not have to absolutely crush the microneedles flat to render them inoperative, although it could be designed to do so, if desired. In FIG. 32, the protrusion does not move, and it is the action of the moving tape/web 516 that causes the microneedles to be broken against the lower-left corner (in this view) of the protrusion 546. Alternatively, the protrusion 546 could be pivotable or otherwise movable so as to crush down (or at an angle) against the microneedles once they move past the window 522. Further alternative mechanical structures could operate as a shear deflection member (similar to the structure 546), or a reciprocal crushing member (not shown) that would crush straight down, at an angle that is normal (i.e., 90 degrees) to the base of the microneedles (or parallel to the microneedles themselves).

In these various alternative embodiments, the mechanical force action could be limited to breaking or crushing the microneedles to a shorter length, or could be allowed to crush the microneedles flat entirely against their base structure. In both cases, the microneedles could be made inoperative, such that they could not be re-used to penetrate the stratum corneum of skin.

Figures 33, 34:
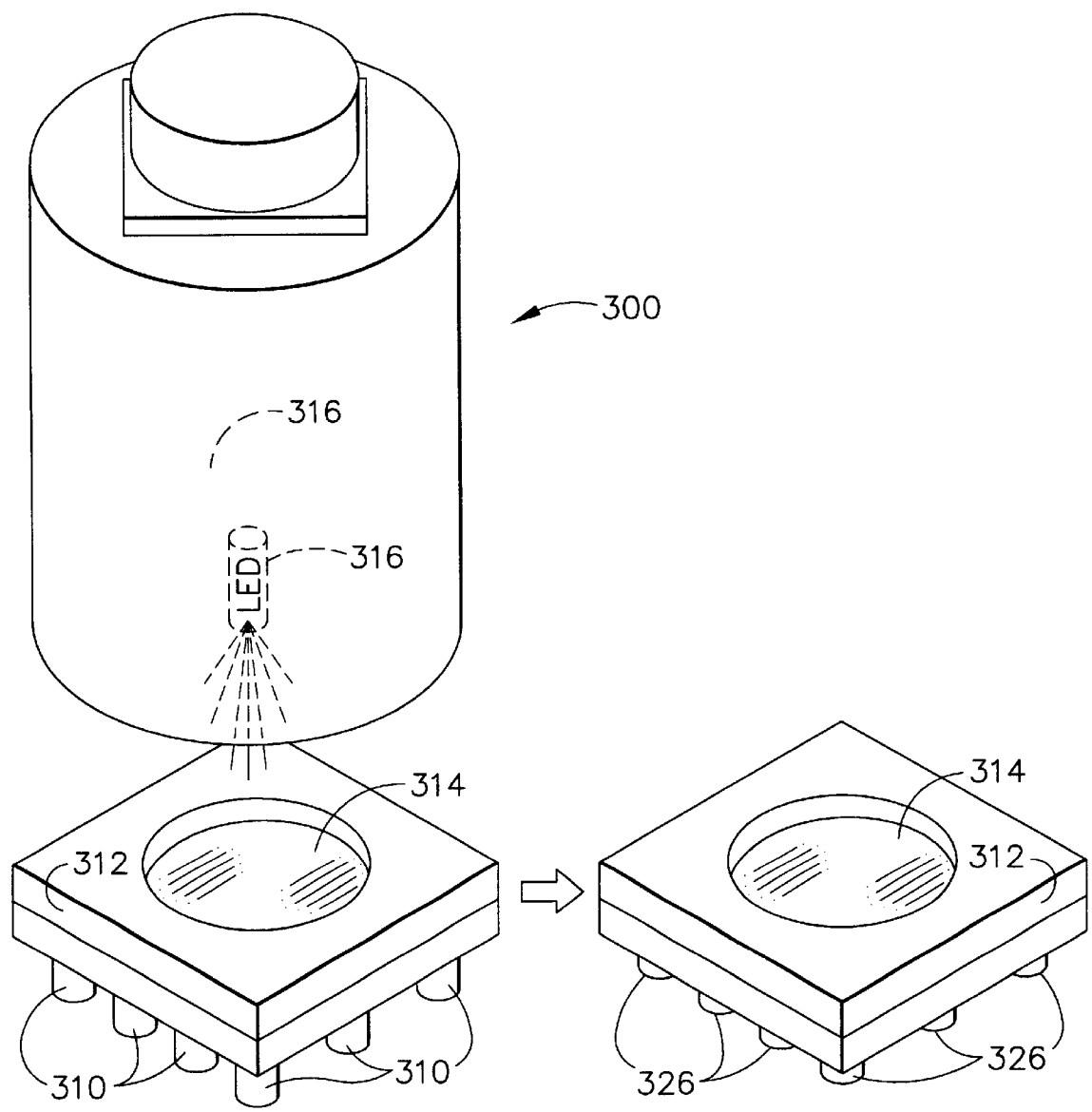
FIG. 33 is a perspective view of single-use microneedle strip system that contains an array of microneedles that are automatically destroyed or deformed after a single use by a user, as constructed according to the principles of the present invention.
FIG. 34 is a perspective view of a microneedle patch from the single-use microneedle strip system of FIG. 33, after the microneedles have been destroyed or deformed.

FIG. 33 illustrates an alternative system used to provide a single-use microneedle patch. The LED 316 that illuminates an optical pad 318 (see FIG. 14) can also provide an increased energy output to raise the temperature of the microneedles 310 of the microneedle array structure. Alternatively, a second, separate light source (not shown) could be used for this purpose, if desired. For example, a laser diode or other laser light source could be used to direct collimated electromagnetic energy (i.e., light) onto the microneedles.

In the embodiment of FIG. 33, the microneedles 310 are preferably substantially transparent to the wavelength of light that is used to detect the concentration of a biological fluid, but not entirely transparent to the wavelength of light that is designed to raise the temperature of those same microneedles. In this manner, the radiant energy (of the second wavelength) can be supplied in a sufficient magnitude to at least partially melt the microneedles 310. The result is illustrated in FIG. 34, as depicted by the deformed microneedles 326 which have been partially melted and thus shortened. In this shortened configuration, the microneedles 326 cannot penetrate the stratum corneum of skin, thereby being rendered useless. If the sampling device 300 automatically effectively destroys the microneedles after taking a sample, then these microneedles 310 become "single-use" microneedles.

It will be understood that the destructive action enabled by the illustrated embodiments of FIGS. 29–34 could be implemented in many other shapes or sizes than illustrated in these views, without departing from the principles of the present invention. Certainly other types of heating arrangements could be utilized, including heat produced by radiation (FIGS. 33–34), such as a small lamp or a laser light source that shines on the microneedles when it is time for them to be disabled. Alternatively, a chemical action (not shown) could be utilized to destroy or partially deform the microneedles. In this instance, the chemicals would be applied just after the microneedle array/patch had advanced past the window 522.

Moreover, it will be understood that the drawings of this patent document are not to scale, and have been specifically altered to show the microneedles as appearing much larger than reality with respect to a person's hand or arm, all for the purpose of clarification of the inventive concepts therein. Both the microneedle lengths and diameters have been greatly expanded in these drawings, as well as the spacings between the individual microneedles. Furthermore, the shapes of the microneedles have generally been depicted as being cylindrical. This is not necessarily the best shape for many applications of microneedles, but has been used herein solely for simplification of the drawings. Other microneedle shapes may be more effective, and are contemplated by the inventors. Some alternative shapes have been disclosed in a patent application assigned to The Procter & Gamble Company, under Ser. No. 09/580,780, filed on May 26, 2000, and titled, "Intracutaneous Edged Microneedle Apparatus." This other patent application is incorporated herein by reference in its entirety.

Another preferred embodiment of the present invention involves the application of heat to facilitate interstitial fluid extraction, or to provide a chemical enhancement at the microneedles to either assist in sensing the interstitial fluid or to facilitate interstitial fluid extraction. In one embodiment, an electrical current can be directed through the tips of microneedles, for example, while they are inserted in the stratum corneum of skin, which will produce heat energy in tips that are made of an electrically conductive material, or of an electrically semiconductive material. The temperature rise of the microneedle tips will assist in extracting the interstitial fluid (ISF) because the heat compromises the cells to create adema that causes a localized fluid collection reaction.

One preferred methodology for using heated tip microneedles is as follows: (1) the microneedles are inserted into the skin, through the stratum corneum; (2) an electrical current is applied so as to run through the tips of the microneedles and thereby raise the temperature of these tips; and (3) a pump mechanism is actuated to extract the interstitial fluid into a receiving reservoir. The pump mechanism can be akin to that described in FIGS. 1–9 (essentially in any suitable shape or size for a particular application). The electrical current can be provided via conductive pathways that bring the current directly to the microneedle tips, akin to the conductive pathways 532 and 536 on FIGS. 29 and 30 (although, of course, the object here is not to melt the microneedles during this procedure).

The electrical current that is applied to the microneedle tips can be a fairly steady direct current, or more preferably can be a pulsed current (of relatively short pulse-widths) that will provide multiple temporary localized heating events in the interstitial fluid adjacent or proximal to these tips. The exact voltage and current levels of these pulses can be varied according to a particular ISF extraction application.

The microneedle tips themselves can be constructed of a metallic material, a semiconductive material, or can be of a plastic material that is coated with a metallic or semiconductive material layer (for example, in a configuration as discussed above in reference to FIG. 12). The coating layer 216 in FIG. 12 can be of a purely electrically conductive material, or more preferably can be of a more resistive material that will generate heat due to $I^2R$ losses as the current passes therethrough. As an alternative, the coating layer 216 (or the entire microneedle tip, for that matter) could be made of a semiconductive material that will exhibit some resistive loss characteristics when the current is passed therethrough. In either configuration, the $I^2R$ losses can create the desired adema in the cells when a proper amount of heat is generated.

In an alternative construction, solid microneedles can be coated with a chemical layer that can absorb some of the interstitial fluid, as illustrated in FIG. 12 by a coating material layer 216. In this configuration, the coating could consist of collagen or albumine, for example. Some of the interstitial fluid can be absorbed by such (or similar) coatings, and cause a chemical, electrochemical, or optochemical reaction to occur at the microneedle tips. In the case of solid microneedles, an electrochemical reaction produced by such a device could provide an electrical output to one or more electrodes 214 (see FIG. 11). Alternatively, either a chemical reaction or an electrochemical reaction could be provided to an optical sensor pad, such as that described in reference to FIGS. 14–17. An example of an optochemical reaction would be a material that exhibits a chemiluminescent or fluorescent characteristic.

An a further alternative construction, hollow microneedles can be coated with a chemical that can absorb some of the interstitial fluid, or more preferably which will facilitate movement of the interstitial fluid through the hollow tubular openings in the microneedles, thereby assisting in ISF extraction. After passing through the microneedles, the fluid can be directed to a receiving reservoir, to an optical sensor pad, or perhaps directly to an electrochemical sensor device that can produce an electrical signal output. In any event, the chemical coating will either enhance movement of the interstitial fluid through the hollow microneedles, or will tend to absorb some of the interstitial fluid in a manner similar to the solid coated microneedles described above in the previous paragraph.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A fluid sampling apparatus, comprising:
   (a) a plurality of microneedles accessible on a first surface of said fluid sampling apparatus;
   (b) a manually-operated pumping apparatus accessible on a second surface of said fluid sampling apparatus; and (c) a reservoir that is in hydraulic communication with both said plurality of microneedles and said pumping apparatus;

wherein said reservoir receives fluid that flows through said plurality of microneedles upon manual actuation of said pumping apparatus, wherein said fluid sampling apparatus has a fluidic passageway that is in hydraulic communication with said plurality of microneedles and said reservoir; and wherein said first surface is located on a first end of said fluid sampling apparatus, and said second surface is located on a second end of said fluid sampling apparatus that is distal from said first end, and wherein said fluid sampling apparatus further comprises a fluidic output port that facilitates communication with an external electrochemical sensor.

2. A fluid sampling apparatus, comprising:

(a) a plurality of microneedles accessible on a first surface of said fluid sampling apparatus;

(b) a manually-operated pumping apparatus accessible on a second surface of said fluid sampling apparatus; and (c) a reservoir that is in hydraulic communication with both said plurality of microneedles and said pumping apparatus;

wherein said reservoir receives fluid that flows through said plurality of microneedles upon manual actuation of said pumping apparatus, wherein said first surface is located on a first side of said fluid sampling apparatus, and said second surface is located on a second side of said fluid sampling apparatus, in which said first side is opposite from said second side, wherein said fluid sampling apparatus further comprises (a) a member having a first end proximal to said reservoir and extending to a second end distal from said reservoir, (b) at least one electrode positioned on said extending member, and (c) a sensor pad that is in hydraulic communication with said reservoir; and wherein said at least one electrode is in communication with said sensor pad, and wherein said fluid sampling apparatus further comprises an electrical interface that converts an output of said sensor pad into an electrical signal; a processing circuit that detects a value of said electrical signal and generates an output signal; and a display device that indicates a value representative of said output signal.

3. A fluid sensing apparatus, comprising:

(a) a plurality of solid microneedles accessible on a first surface of said fluid sensing apparatus, said solid microneedles being coated on an exterior surface; whereupon said solid microneedles making contact with a biological barrier, said coating on said microneedles acting as an transducer responsive to a property of a fluid of said biological barrier, and thereby generating an electrical signal in response to said fluid property;

(b) a member having a first end proximal to said coated microneedles and extending to a second end distal from said coated microneedles; and (c) at least one electrode positioned on said extending member, wherein said at least one electrode is in communication with said coated microneedles, wherein said fluid sensing apparatus further comprises an electrical interface that converts an output of said at least one electrode into an electrical signal; a processing circuit that detects a value of said electrical signal and generates an output signal; and a display device that indicates a value of said output signal.

4. The fluid sensing apparatus as recited in claim 3, wherein said processing circuit acquires a single reading from said transducer, thereby effectively implementing a one-touch reading system.

5. The fluid sensing apparatus as recited in claim 3, wherein said processing circuit acquires multiple readings from said transducer over a time interval, thereby effectively implementing a continuous measurement system.

6. The fluid sensing apparatus as recited in claim 5, wherein said processing circuit stores said multiple readings in a memory device, used in a later retrieval for trend analysis, or to be communicated to a remote device.

7. The fluid sensing apparatus as recited in claim 6, wherein said multiple readings represent one of: raw data, averages, arithmetic means, maxima or minima.

8. A fluid sampling apparatus, comprising:

(a) an attachable/detachable portion that includes a plurality of microneedles, a reservoir, an optical sensor pad, and an optical window; and (b) a main body portion that includes a receptacle to receive said attachable/detachable portion such that, when in position, the optical window faces said main body portion and the plurality of microneedles are accessible; a light source and light detector; and a manually-operated control actuator mounted on a surface of said main body portion that causes fluid to flow proximal to said plurality of microneedles;

wherein said reservoir receives fluid that flows through said plurality of microneedles upon manual operation of said control actuator, and said optical sensor pad exhibits a change in a physical property that is detected by said light detector as said light source shines light upon said optical sensor pad.

9. The fluid sampling apparatus as recited in claim 8, wherein said manually-operated pumping apparatus comprises a pushbutton-like device, which: (a) is actuated at least once to cause a pressure differential that withdraws fluid through said microneedles, or (b) is pre-cocked in a first position, and then released by said manual actuation to move to a second position that causes cause a pressure differential that withdraws fluid through said microneedles.

10. The fluid sampling apparatus as recited in claim 8, further comprising: a display device that indicates a value representative of an output signal produced by said light detector, or which displays a message to the user.

11. The fluid sampling apparatus as recited in claim 8, further comprising: an electrical circuit that provides electrical current to tips of said microneedles, thereby heating said microneedle tips while the microneedles are inserted in skin to facilitate extraction of interstitial fluid.

12. The fluid sampling apparatus as recited in claim 8, further comprising: a coating layer of material on tips of said plurality of microneedles, said coating layer absorbing some interstitial fluid of skin, and producing a chemical, electrochemical, or optochemical reaction thereto.

13. A fluid sampling apparatus, comprising:

(a) an attachable/detachable portion that includes a plurality of microneedles, a reservoir, an electrochemical sensor pad, and at least one electrode in communication with said sensor pad; and (b) a main body portion that includes a receptacle to receive said attachable/detachable portion such that, when in position, the at least one electrode faces said main body portion and the plurality of microneedles are accessible; an electrical sensor; and a manually-operated pumping apparatus accessible on a surface of said main body portion;

wherein said reservoir receives fluid that flows through said plurality of microneedles upon manual actuation of said pumping apparatus, and said electrochemical sensor pad exhibits a change in a physical property that is detected by said at least one electrode which outputs an electrical signal, and said electrical sensor is in communication with said at least one electrode and generates an output signal in response to said electrical signal, and wherein said fluid sampling apparatus further comprises a display device that indicates a value representative of said output signal produced by said electrical sensor, or which displays a message to the user.

14. A fluid sampling apparatus, comprising:

a plurality of microneedles and an associated substrate that is in mechanical communication with a plunger, said plunger being manually operable; a housing that contains a variable volume chamber and which contains a flexible membrane that deflects upon movement of said plunger, said membrane's deflection causing a variation in the volume of said chamber; and an output port that is in hydraulic communication with said variable volume chamber;

wherein upon actuation of said plunger in one direction, said microneedles being pushed into and piercing a biological barrier; and upon actuation of said plunger in a second, opposite direction, fluid from said biological barrier is withdrawn into said variable volume chamber and thereby directed to said output port, wherein said fluid sampling apparatus further comprises a sensor that generates an electrical signal in response to a change in a property of said fluid after said fluid travels through a tube that is in hydraulic communication with said output port, and a display device that indicates a value of said electrical signal produced by said sensor, or which displays a message to the user.

15. A replaceable cartridge, comprising:

a plurality of microneedle strips attached to a movable substrate of material, each of said microneedle strips including: a plurality of microneedles accessible to a user, a sensor that is in communication with a fluid that flows through said microneedles, and a signal transducer that is in communication with said sensor;

wherein said signal transducer of a first of the plurality of microneedle strips generates an electrical signal that is communicated to an output port, and wherein said movable substrate of material is indexable to a next position that will make a second of the plurality of microneedle strips accessible to a user.

16. The replaceable cartridge as recited in claim 15, wherein said movable substrate of material comprises a web of material that moves from a source reel to a take-up reel, upon indexing of the substrate.

17. The replaceable cartridge as recited in claim 15, wherein said movable substrate of material comprises a circular disc that contains said plurality of microneedle strips near the disc's outer diameter.

18. The replaceable cartridge as recited in claim 15, wherein said signal transducer comprises one of: (a) at least one electrode, (b) an electron sensor, or (c) an optical coupler.

19. The replaceable cartridge as recited in claim 15, further comprising:

(a) a signal conditioning circuit that converts said electrical signal generated by said signal transducer into a second signal;

(b) a personal data assistant that has an electrical plug-in port that attachably/detachably mates with said output port, and receives said second signal from said cartridge; said personal data assistant including a processing circuit, a memory circuit, a display controller circuit, and a visible display that is discernible by a human eye; and said personal data assistant including a computer program that measures a property of said second signal and displays a corresponding numeric quantity.

20. The replaceable cartridge as recited in claim 19, wherein said second signal comprises one of: (a) an electrical signal, (b) an acoustic signal, (c) a magnetic signal, or (d) an electromagnetic signal having a wavelength so as to be one of: (i) an optical signal, (ii) a microwave signal, or (iii) a radio-frequency signal.

21. The replaceable cartridge as recited in claim 15, further comprising:

(a) a signal conditioning circuit that converts said electrical signal generated by said signal transducer into a second signal;

(b) a self-contained display unit which comprises: an electrical plug-in port that attachably/detachably mates with said output port, and receives said second signal from said cartridge, a processing circuit, a memory circuit, a display controller circuit, and a visible display that is discernible by a human eye; and a computer program that measures a property of said second signal and displays a corresponding numeric quantity.

22. The replaceable cartridge as recited in claim 21, wherein said second signal comprises one of: (a) an electrical signal, (b) an acoustic signal, (c) a magnetic signal, or (d) an electromagnetic signal having a wavelength so as to be one of: (i) an optical signal, (ii) a microwave signal, or (iii) a radio-frequency signal.

23. The replaceable cartridge as recited in claim 21, further comprising: a manually-operable actuator that advances said movable, indexable substrate of material to said next position.

24. The replaceable cartridge as recited in claim 21, further comprising: a discharge port where spent microneedle strips are automatically ejected after said movable, indexable substrate of material has been advanced to said next position.

25. A single-use microneedle system, comprising:

an array of microneedle members that protrude from a base member, said microneedle members being of a size, shape, and material so as to penetrate through a stratum corneum of skin when placed against said skin; and a self-destruct mechanism that renders said microneedle members incapable of penetrating said stratum corneum after being operative upon said microneedle members, said self-destruct mechanism comprising one of: (a) a heat source, (b) an electrical energy source, (c) a optical energy source, (d) a chemical reaction, (e) a mechanical member that exerts a force, or (f) a material that permanently encapsulates the microneedle members.

26. The single-use microneedle system as recited in claim 25, wherein said self-destruct mechanism either melts, chemically alters, or mechanically alters said array of microneedle members so as to: (a) shorten a length of the array of microneedle members to an extent that they cannot penetrate entirely through said stratum corneum, (b) deform a shape of a tip or a side wall of said array of microneedle members to an extent that they cannot sufficiently pierce said stratum corneum, or (c) break or crush said array of microneedle members flat entirely against said base member.

27. The single-use microneedle system as recited in claim 25, wherein said heat source comprises: an electrical heating element, a electrical lamp, a laser light source, or a chemical reaction.

28. The single-use microneedle system as recited in claim 25, wherein said mechanical member comprises one of: (a) a pivotable crushing member, (b) a shear deflection member, (c) a reciprocal crushing member, or (d) a mechanical flattening structure; and wherein said mechanical member either breaks or crushes said array of microneedle members.

29. The single-use microneedle system as recited in claim 25, wherein said array of microneedle members are either solid or hollow.

30. The single-use microneedle system as recited in claim 25, further comprising: a replaceable cartridge that contains a plurality of said array of microneedle members attached to a movable substrate of material, said cartridge having an opening that allows a first one of said plurality of said array of microneedle members to be accessible to a user; wherein said movable substrate of material indexes to a next position that will make a second one of the plurality of said array of microneedle members accessible to a user, and wherein said first one of the plurality of said array of microneedle members simultaneously automatically indexes to said self-destruct mechanism, where said first one of the plurality of said array of microneedle members is rendered incapable of penetrating said stratum corneum.

* * * * *